(12) United States Patent
Assell et al.

(10) Patent No.: US 9,833,328 B2
(45) Date of Patent: Dec. 5, 2017

(54) SYSTEM AND METHODS FOR FACET JOINT TREATMENT

(71) Applicant: Zyga Technology, Inc., Minnetonka, MN (US)

(72) Inventors: Robert L. Assell, St. Paul, MN (US); Brian P. Beaubien, St. Paul, MN (US); David W. Stassen, Edina, MN (US)

(73) Assignee: Zyga Technology, Minnetonka, MN (US)

( * ) Notice: Subject to any disclaimer, the term of this patent is extended or adjusted under 35 U.S.C. 154(b) by 568 days.

(21) Appl. No.: 14/592,822

(22) Filed: Jan. 8, 2015

(65) Prior Publication Data

US 2015/0119988 A1 Apr. 30, 2015

Related U.S. Application Data

(60) Division of application No. 13/678,535, filed on Nov. 15, 2012, now Pat. No. 9,233,006, and a
(Continued)

(51) Int. Cl.
*A61F 2/44* (2006.01)
*A61F 2/46* (2006.01)
*A61F 2/30* (2006.01)

(52) U.S. Cl.
CPC ........ *A61F 2/4405* (2013.01); *A61F 2/30767* (2013.01); *A61F 2/4611* (2013.01);
(Continued)

(58) Field of Classification Search
CPC ..................................................... A61F 2/4405
See application file for complete search history.

(56) References Cited

U.S. PATENT DOCUMENTS 2,677,369 A 5/1954 Knowles
3,426,364 A 2/1969 Lumb
(Continued)

FOREIGN PATENT DOCUMENTS

DE 9304368 5/1995
DE 201 12 123 U1 9/2001
(Continued)

OTHER PUBLICATIONS

"Dynesys® Dynamic Stabiliation System: A Guide for Patients", 5 pages, as listed on http://www.zimmer.com/ctl? template=IN&action=1=&op=global&id=9163&pr=Y on Mar. 8, 2007, however, the document lists the most recent update as Jul. 21, 2005.
(Continued)

*Primary Examiner* — David Bates
(74) *Attorney, Agent, or Firm* — Michael A. Bondi; Moss & Barnett

(57) ABSTRACT

A method of resurfacing a facet joint with a facet implant system. The facet joint includes a superior facet and an inferior facet that are adjacent to each other and movable with respect to each other. A first facet implant component is provided that has a first visualization marker. The first visualization marker includes a first marker section and a second marker section. The first marker section is oriented at an angle with respect to the second marker section. The first facet implant component between the superior facet and the inferior facet. A location and an orientation of the first facet implant component are determined using an imaging technique that locates the first visualization marker.

19 Claims, 14 Drawing Sheets

Related U.S. Application Data continuation-in-part of application No. 13/084,104, filed on Apr. 11, 2011, now Pat. No. 8,663,293.

(60) Provisional application No. 61/355,140, filed on Jun. 15, 2010.

(52) U.S. Cl.
CPC . *A61F 2002/3008* (2013.01); *A61F 2002/308* (2013.01); *A61F 2002/30056* (2013.01); *A61F 2002/30113* (2013.01); *A61F 2002/30321* (2013.01); *A61F 2002/30322* (2013.01); *A61F 2002/30324* (2013.01); *A61F 2002/30795* (2013.01); *A61F 2002/30822* (2013.01); *A61F 2002/30828* (2013.01); *A61F 2002/30841* (2013.01); *A61F 2002/30904* (2013.01); *A61F 2002/4623* (2013.01)

(56) References Cited

U.S. PATENT DOCUMENTS

| | | |
|---|---|---|
| 3,879,767 A | 4/1975 | Stubstad |
| 4,034,746 A | 7/1977 | Williams |
| 4,052,753 A | 10/1977 | Dedo |
| 4,349,921 A | 9/1982 | Kuntz |
| 4,502,161 A | 3/1985 | Wall |
| 4,553,273 A | 11/1985 | Wu |
| 4,554,914 A | 11/1985 | Kapp |
| 4,599,086 A | 7/1986 | Doty |
| 4,636,217 A | 1/1987 | Ogilvie |
| 4,742,256 A | 5/1988 | Brantigan |
| 4,834,757 A | 5/1989 | Brantigan |
| 4,877,020 A | 10/1989 | Vich |
| 5,092,866 A | 3/1992 | Breard et al. |
| 5,147,404 A | 9/1992 | Downey |
| 5,156,616 A | 10/1992 | Meadows et al. |
| 5,415,659 A | 5/1995 | Lee |
| 5,415,661 A | 5/1995 | Holmes |
| 5,496,318 A | 3/1996 | Howland et al. |
| 5,507,823 A | 4/1996 | Walstron |
| 5,527,312 A | 6/1996 | Ray |
| 5,565,122 A | 10/1996 | Zinnbauer et al. |
| 5,571,191 A * | 11/1996 | Fitz .................. A61F 2/4405 606/247 |
| 5,609,634 A | 3/1997 | Voydeville |
| 5,665,122 A | 9/1997 | Kambin |
| 5,681,310 A | 10/1997 | Yuan et al. |
| 5,683,464 A | 11/1997 | Wagner |
| 5,697,889 A | 12/1997 | Slotman |
| RE36,221 E | 6/1999 | Breard et al. |
| 5,968,098 A | 10/1999 | Winslow |
| 6,019,792 A | 2/2000 | Cauthen |
| RE36,758 E | 6/2000 | Fitz |
| 6,102,948 A | 8/2000 | Brosnahan, III |
| 6,126,688 A | 10/2000 | McDonnell |
| 6,132,464 A | 10/2000 | Martin |
| 6,132,468 A | 10/2000 | Mansmann |
| 6,156,067 A | 12/2000 | Bryan et al. |
| 6,179,874 B1 | 1/2001 | Cauthen |
| 6,287,313 B1 | 9/2001 | Sasso |
| 6,290,724 B1 | 9/2001 | Marino |
| 6,368,350 B1 | 4/2002 | Erickson et al. |
| 6,440,168 B1 | 8/2002 | Cauthen |
| 6,443,988 B2 | 9/2002 | Felt |
| 6,458,159 B1 | 10/2002 | Talgott |
| 6,485,518 B1 | 11/2002 | Cornwall et al. |
| 6,540,747 B1 | 4/2003 | Marino |
| 6,544,265 B2 | 4/2003 | Lieberman |
| 6,562,046 B2 | 5/2003 | Sasso |
| 6,610,093 B1 | 8/2003 | Pisharodi |
| 6,652,585 B2 | 11/2003 | Lange |
| 6,652,587 B2 | 11/2003 | Felt |
| 6,679,915 B1 | 1/2004 | Cauthen |
| 6,733,531 B1 | 5/2004 | Trieu |
| 6,846,328 B2 | 1/2005 | Cauthen |
| 6,893,463 B2 | 5/2005 | Fell |
| 6,932,842 B1 | 8/2005 | Litschko |
| 6,966,930 B2 | 11/2005 | Arnin et al. |
| 6,974,478 B2 | 12/2005 | Reiley et al. |
| 6,986,771 B2 | 1/2006 | Paul |
| 6,989,011 B2 | 1/2006 | Paul |
| 7,001,431 B2 | 2/2006 | Bao |
| 7,041,136 B2 | 5/2006 | Goble et al. |
| 7,087,084 B2 | 8/2006 | Reiley |
| 7,101,398 B2 | 9/2006 | Dooris |
| 7,115,131 B2 | 10/2006 | Engh |
| 7,115,132 B2 | 10/2006 | Errico |
| 7,115,142 B2 | 10/2006 | Muhanna |
| 7,146,665 B1 | 12/2006 | Bryan et al. |
| 7,189,240 B1 | 3/2007 | Dekel |
| 7,270,681 B2 | 9/2007 | Cauthen |
| 7,291,169 B2 | 11/2007 | Hodorek |
| 7,371,238 B2 | 5/2008 | Soboleski |
| 7,377,942 B2 | 5/2008 | Berry |
| 7,468,075 B2 | 12/2008 | Lang |
| 7,476,252 B2 | 1/2009 | Foley |
| 7,591,851 B2 | 9/2009 | Winslow et al. |
| 7,618,451 B2 | 11/2009 | Berez |
| 7,708,761 B2 | 5/2010 | Petersen |
| 7,744,612 B2 | 6/2010 | Blain |
| 7,776,090 B2 | 8/2010 | Winslow |
| 7,846,183 B2 | 12/2010 | Blain |
| 7,922,766 B2 | 4/2011 | Grob |
| 7,927,374 B2 | 4/2011 | Duggal |
| 7,935,134 B2 | 5/2011 | Reglos et al. |
| 7,938,836 B2 | 5/2011 | Ainsworth et al. |
| 7,938,857 B2 | 5/2011 | Garcia Bengochea et al. |
| 7,955,355 B2 | 5/2011 | Chin |
| 7,998,172 B2 | 8/2011 | Blain |
| 8,100,955 B2 | 1/2012 | Blain |
| 8,343,189 B2 | 1/2013 | Assell et al. |
| 8,425,558 B2 * | 4/2013 | McCormack ........ A61B 17/025 606/247 |
| 2001/0051807 A1 | 12/2001 | Grafton |
| 2002/0026244 A1 | 2/2002 | Trieu |
| 2002/0055737 A1 | 5/2002 | Lieberman |
| 2002/0120270 A1 | 8/2002 | Trieu et al. |
| 2002/0143329 A1 | 10/2002 | Serhan et al. |
| 2002/0151895 A1 | 10/2002 | Soboleski |
| 2003/0028250 A1 | 2/2003 | Reiley et al. |
| 2003/0176871 A1 | 9/2003 | Pavlov et al. |
| 2003/0208202 A1 | 11/2003 | Falahee |
| 2003/0220643 A1 | 11/2003 | Feree |
| 2004/0010312 A1 | 1/2004 | Enayati |
| 2004/0049280 A1 | 3/2004 | Cauthen |
| 2004/0087954 A1 | 5/2004 | Allen et al. |
| 2004/0143332 A1 | 7/2004 | Krueger |
| 2004/0153159 A1 | 8/2004 | Cauthen |
| 2004/0225360 A1 | 11/2004 | Malone |
| 2004/0236328 A1 | 11/2004 | Paul et al. |
| 2004/0143333 A1 | 12/2004 | Ferree |
| 2004/0260287 A1 | 12/2004 | Ferree |
| 2005/0021029 A1 | 1/2005 | Trieu et al. |
| 2005/0027361 A1 | 2/2005 | Reiley et al. |
| 2005/0049705 A1 | 3/2005 | Hale et al. |
| 2005/0076974 A1 | 4/2005 | Blain |
| 2005/0080486 A1 | 4/2005 | Fallin et al. |
| 2005/0085912 A1 | 4/2005 | Arnin et al. |
| 2005/0119748 A1 | 6/2005 | Reiley et al. |
| 2005/0125062 A1 | 6/2005 | Biedermann |
| 2005/0143818 A1 | 6/2005 | Yuan et al. |
| 2005/0143825 A1 | 6/2005 | Enayati |
| 2005/0159746 A1 * | 7/2005 | Grob .................. A61B 17/1671 606/247 |
| 2005/0177240 A1 | 8/2005 | Blain |
| 2005/0197700 A1 | 9/2005 | Boehm |
| 2005/0197706 A1 | 9/2005 | Hovorka |
| 2005/0251256 A1 | 11/2005 | Reiley |
| 2005/0273100 A1 | 12/2005 | Taylor |
| 2006/0009847 A1 | 1/2006 | Reiley |
| 2006/0036243 A1 | 2/2006 | Sasso |
| 2006/0036323 A1 | 2/2006 | Carl et al. |
| 2006/0041311 A1 | 2/2006 | McLeer |

(56) References Cited

U.S. PATENT DOCUMENTS

| | | |
|---|---|---|
| 2006/0064099 A1 | 3/2006 | Pavlov et al. |
| 2006/0084977 A1 | 4/2006 | Lieberman |
| 2006/0085068 A1 | 4/2006 | Barry |
| 2006/0089633 A1 | 4/2006 | Bleich et al. |
| 2006/0100705 A1 | 5/2006 | Puno |
| 2006/0111779 A1 | 5/2006 | Peterson |
| 2006/0111780 A1 | 5/2006 | Peterson |
| 2006/0111781 A1 | 5/2006 | Petersen |
| 2006/0111782 A1 | 5/2006 | Petersen |
| 2006/0116768 A1 | 6/2006 | Krueger |
| 2006/0122701 A1 | 6/2006 | Kiester |
| 2006/0149374 A1 | 7/2006 | Winslow et al. |
| 2006/0155297 A1 | 7/2006 | Ainsworth |
| 2006/0190081 A1 | 8/2006 | Kraus et al. |
| 2006/0217754 A1 | 9/2006 | Boehm, Jr. et al. |
| 2006/0235391 A1 | 10/2006 | Sutterlin, III |
| 2006/0235403 A1 | 10/2006 | Blain |
| 2006/0235409 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2006/0241648 A1 | 10/2006 | Bleich et al. |
| 2006/0241758 A1 | 10/2006 | Peterman et al. |
| 2006/0247632 A1 | 11/2006 | Winslow |
| 2006/0247633 A1 | 11/2006 | Winslow et al. |
| 2006/0276790 A1 | 12/2006 | Dawson et al. |
| 2006/0276907 A1 | 12/2006 | Boyer, II et al. |
| 2007/0032790 A1 | 2/2007 | Aschmann et al. |
| 2007/0055236 A1 | 3/2007 | Hudgins et al. |
| 2007/0055252 A1 | 3/2007 | Blain |
| 2007/0055373 A1 | 3/2007 | Hudgins et al. |
| 2007/0067032 A1 | 3/2007 | Felt et al. |
| 2007/0083265 A1 | 4/2007 | Malone |
| 2007/0083266 A1 | 4/2007 | Lang |
| 2007/0088358 A1 | 4/2007 | Yuan et al. |
| 2007/0018218 A1 | 5/2007 | Hooper |
| 2007/0100450 A1 | 5/2007 | Hodorek |
| 2007/0118218 A1 | 5/2007 | Hooper |
| 2007/0123863 A1 | 5/2007 | Winslow et al. |
| 2007/0135814 A1 | 6/2007 | Farris |
| 2007/0135919 A1 | 6/2007 | Aebi et al. |
| 2007/0149976 A1 | 6/2007 | Hale et al. |
| 2007/0161991 A1 | 7/2007 | Altarac et al. |
| 2007/0167946 A1 | 7/2007 | Triplett et al. |
| 2007/0179608 A1 | 8/2007 | Ek et al. |
| 2007/0225813 A1 | 9/2007 | Haines |
| 2007/0276370 A1 | 11/2007 | Altarac et al. |
| 2007/0276498 A1 | 11/2007 | Aebi et al. |
| 2007/0276499 A1 | 11/2007 | Paul et al. |
| 2008/0009875 A1 | 1/2008 | Sankaran |
| 2008/0027543 A1 | 1/2008 | Eisermann |
| 2008/0027547 A1 | 1/2008 | Yu |
| 2008/0033440 A1 | 2/2008 | Moskowitz et al. |
| 2008/0045954 A1 | 2/2008 | Reiley et al. |
| 2008/0051901 A1 | 2/2008 | De Villiers |
| 2008/0091199 A1 | 4/2008 | Cragg |
| 2008/0097613 A1 | 4/2008 | Reiley |
| 2008/0119933 A1 | 5/2008 | Aebi et al. |
| 2008/0125814 A1 | 5/2008 | Yuan et al. |
| 2008/0132951 A1 | 6/2008 | Reiley et al. |
| 2008/0140121 A1 | 6/2008 | McLeer |
| 2008/0143818 A1 | 6/2008 | Ferren |
| 2008/0154305 A1 | 6/2008 | Foley et al. |
| 2008/0208249 A1 | 8/2008 | Blain |
| 2008/0262555 A1 | 10/2008 | Assell et al. |
| 2009/0036926 A1* | 2/2009 | Hestad ............... A61B 17/7064 606/247 |
| 2009/0062920 A1 | 3/2009 | Tauber |
| 2009/0088846 A1 | 4/2009 | Myung |
| 2009/0138053 A1 | 5/2009 | Assell et al. |
| 2009/0177205 A1 | 7/2009 | McCormack et al. |
| 2009/0234458 A1 | 7/2009 | De Villiers |
| 2009/0264928 A1 | 10/2009 | Blain |
| 2010/0131008 A1 | 5/2010 | Overes |
| 2010/0228288 A1 | 9/2010 | Blain |
| 2010/0249937 A1 | 9/2010 | Blain |
| 2010/0274286 A1 | 10/2010 | Blain |
| 2010/0286778 A1 | 11/2010 | Eisermann |
| 2010/0292797 A1 | 11/2010 | Lindner et al. |
| 2011/0022089 A1 | 1/2011 | Assell et al. |
| 2011/0040301 A1 | 2/2011 | Blain |
| 2011/0060366 A1 | 3/2011 | Heim |
| 2011/0082503 A1 | 4/2011 | Blain |
| 2011/0307061 A1 | 12/2011 | Assell et al. |
| 2011/0313456 A1 | 12/2011 | Blain |

FOREIGN PATENT DOCUMENTS

| | | |
|---|---|---|
| DE | 20 2007 015 081 U1 | 1/2008 |
| DE | 20 2009 006 906 U1 | 7/2009 |
| EP | 0 381 588 A1 | 8/1990 |
| FR | 2681525 A1 | 3/1993 |
| FR | 2177675 A1 | 9/1995 |
| WO | 93/10725 A2 | 6/1993 |
| WO | 1994/05235 A1 | 3/1994 |
| WO | 02/034147 A1 | 2/2002 |
| WO | 02/045765 A2 | 6/2002 |
| WO | 02/065954 A1 | 8/2002 |
| WO | 2005/072661 A1 | 8/2005 |
| WO | 2005/076974 A2 | 8/2005 |
| WO | 2006/020464 A2 | 2/2006 |
| WO | 2006/065774 A1 | 6/2006 |
| WO | 2006/096803 A2 | 9/2006 |
| WO | 2007/019215 A2 | 2/2007 |
| WO | 2009/143496 A1 | 11/2009 |
| WO | 2011/011621 A1 | 1/2011 |

OTHER PUBLICATIONS

"Dynesys® Dynamic Stabiliation System", 4 pages, as listed on http://www.zimmer.com/ctl? template=IN&action=1=&op=global &id=9165&pr=Y on Mar. 8, 2007, however, the document lists the most recent update as Jul. 21, 2005.

* cited by examiner

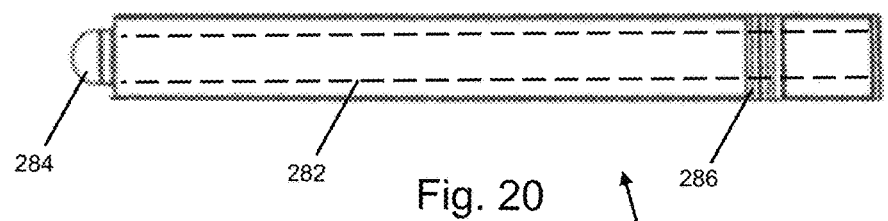
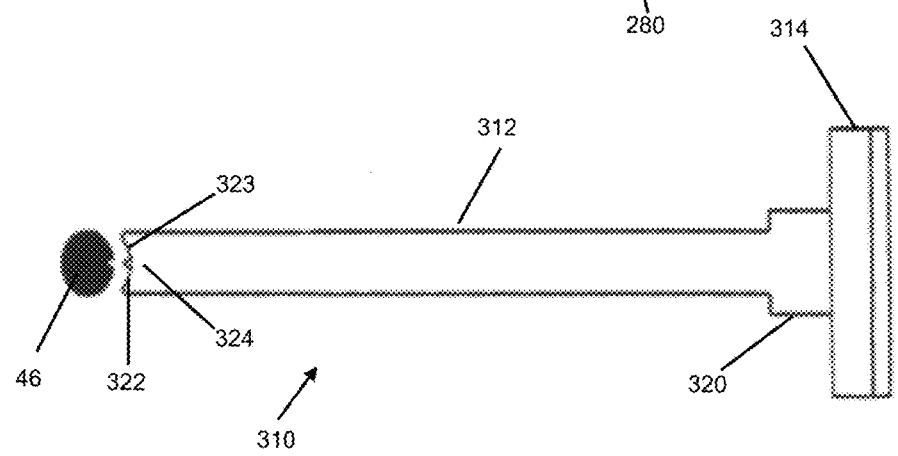
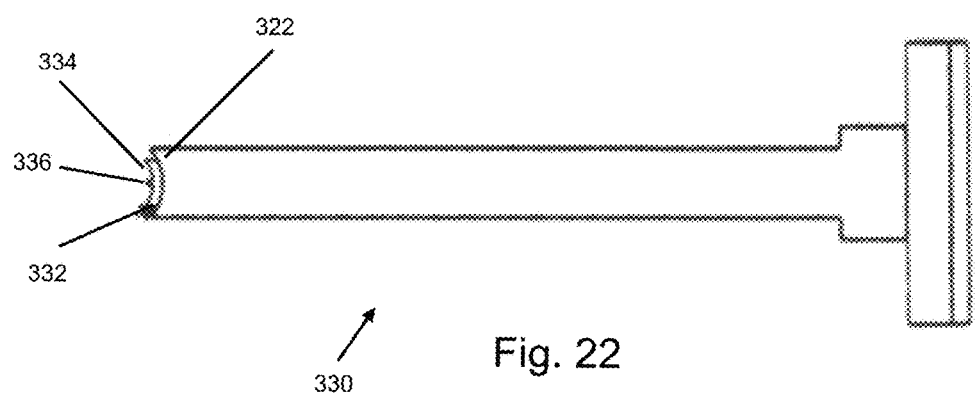

SYSTEM AND METHODS FOR FACET JOINT TREATMENT

REFERENCE TO RELATED APPLICATION

This application is a divisional of U.S. application Ser. No. 13/678,535, which was filed on Nov. 15, 2012, and which is a continuation-in-part of U.S. application Ser. No. 13/084,104, which was filed on Apr. 11, 2011, which claimed priority to U.S. Provisional Application No. 61/355,140, which was filed on Jun. 15, 2010, the contents of which are incorporated herein by reference.

FIELD OF THE INVENTION

An embodiment of the invention relates to a system for treating facet joint pain. More particularly, the invention relates to an implant system for treating facet joint pain.

BACKGROUND OF THE INVENTION

Within the next ten years, more than seventy million people will join the ranks of seniors. In an aging population, the articular cartilage that allows bones to smoothly move over each other wears down with time and disease, and like many tissues in the body, articular cartilage has a limited ability to heal itself.

At this time, options that help to relieve severe degenerative joint pain, or osteoarthritis, include joint replacement or fusion. As examples, approximately 200,000 total knee joint replacement operations and over 300,000 hip joint replacement operations are performed annually. While these operations are generally effective at treating the affected joint, these artificial joint implants typically only last about 10-15 years.

Chronic lower back pain also affects both work force productivity and healthcare expense. There are currently over 500,000 surgical procedures performed annually in the United States in an attempt to alleviate lower back pain even though such surgical procedures are typically only performed after the failure of more conservative therapy such as bed rest, pain and muscle relaxant medication, physical therapy or steroid injection. The source of this pain may originate from dysfunction among a plurality of anatomical structures (as described below) that are comprised in the spine, including facet joints.

To understand spinal biomechanics, and the impacts of dysfunction in therapy, it is useful to first consider the spinal anatomy. The vertebrae of the spine are conventionally subdivided into several sections. Moving from the head (cephalad) to the tailbone (caudal), the sections are cervical, thoracic, lumbar, sacral, and coccygeal.

Regardless of location, each vertebra forms two pedicles and two laminae that combine to define a spinal foramen in which the spinal cord is protected. Extending laterally from the pedicles are two transverse processes. Extending from the mid-line of the vertebra where the two laminae meet is a spinous process. These three processes serve as a connection point for ligaments and muscles.

Adjacent vertebrae are separated by an intervertebral disc and surfaces of the adjacent vertebrae form portions of two facet joints by and between the two vertebrae. Relative to a spinal segment consisting of an intermediate vertebra, an immediately adjacent cephalad vertebra, and an immediately adjacent caudal vertebra, the intermediate vertebra forms portions of four facet joints; namely, two facet joints with the cephalad vertebra, and two facet joints with the caudal vertebra.

With the above background in mind, FIGS. 1A and 1B illustrate a facet joint 20 composed of a superior articular facet 22 and an inferior articular facet 24. The superior articular facet 22 is formed by the vertebral level below the intervertebral disc (i.e., a superior articular facet projects upward from the junction of the lamina and the pedicle), whereas the inferior articular facet 24 is formed by the vertebral level above the intervertebral disc (i.e., an inferior articular facet projects downward).

On the superior articular facet 22 is a superior articular face 26, and on the inferior articular facet 24 is an inferior articular face 28. Facet joints are oriented obliquely to the sagittal plane, and the joint space itself is curved from front to back. The more posteriorly located inferior face 28 is convex, whereas the more interiorly located superior face 26 is concave.

The facet joint 20 is a synovial joint that is defined by the two opposing bony faces 26, 28 with cartilage 30 between them and a capsule 32 around the joint 20. More specifically, synovial fluid 34 is contained inside the joint 20 by the capsule 32, that is otherwise a water-tight sac of soft tissue and ligaments that fully surrounds and encloses the joint 20, and keeps the joint faces 26, 28 lubricated.

The ends of the bone articular facets 22, 24 that make up the synovial facet joint 20 are normally covered with the articular, hyaline cartilage 30 that allows the bony faces 26, 28 to glide against one another, providing the flexibility that allows the movement of vertebral bodies relative to one another.

As indicated above, there are two facet joints between each pair of vertebrae, one on each side (located posterior and lateral of the vertebral centerline), from the top and bottom of each vertebra. The joints combine with the disc space to create a three joint complex at each vertebral level, and each joint extends and overlaps neighboring vertebral facet joints, linking each other and hence the vertebra together.

The assembly of two vertebral bodies, the interposed spinal disc and the attached ligaments, muscles, and facet joints (inferior articulating processes that articulate with the superior articular processes of the next succeeding vertebra in the caudal direction) is referred to as a "spinal motion segment." Each motion segment contributes to the overall flexibility of the spine and contributes to the overall ability of the spine to provide support for the movement of the trunk and head, and in particular, the facet joints limit torsional (twisting) motion.

When the facets of one or more vertebral bodies degenerate or otherwise become damaged such that the vertebrae no longer articulate or properly align with each other, there is a resulting loss of mobility and pain or discomfort. The functional role of the facet joints in a spinal motion segment is thus relevant to an understanding of the operative and functional advantages of the facet joint systems and methods disclosed herein, which achieve dynamic stabilization and mobility preservation without constraining motion in any plane.

As indicated above, facet joints are located on the posterior column of the spine. The context of this discussion: "anterior" refers to in front of the spinal column, and "posterior" refers to behind the column; "cephalad" means towards a patient's head (sometimes referred to as "superior"); and "caudal" (sometimes referred to as "inferior") refers to the direction or location that is closer to the patient's feet.

Facet joints can be arthritic due to degeneration with aging, trauma, or disease (e.g., pathologies that include inflammatory, metabolic, or synovial, disorders). In addition, fractures, torn ligaments, and disc problems (e.g., dehydration or herniation) can all cause abnormal movement and alignment, putting extra stress on the surfaces of the facet joint.

The physiological response to this extra pressure is the development of osteophites, i.e., bone spurs. As the spurs form around the edges of the facet joint, the joint becomes enlarged, a condition called hypertrophy, and eventually the joint surfaces become arthritic. When the articular cartilage degenerates or wears away, the bone underneath is uncovered and rubs against bone. The joint thus becomes inflamed, swollen, and painful.

Facet joint arthritis is a significant source of neck and back pain, and is attributable to about 15-30% of persistent lower back pain complaints. Upon failure of conservative treatment for facet joint pain such as intra-articular steroids/local anesthetic injections administered under fluoroscopic guidance, some patients with chronic pain may eventually require surgical intervention for facet joint arthritis including, for example, facet rhizotomy; facet ectomony to remove the facet joint to reduce pressure on the exiting nerve root; total joint replacement or facet arthrodesis (i.e., fixation leading to fusion, where the two articulating surfaces of the joint remain immobile or grow solidly together and form a single, solid piece of bone); etc.

While these surgical procedures may alleviate back pain, many joint replacements and all fusions do not restore the normal physiological function and motion attributable to healthy anatomical form. Rather, they often significantly alter spinal biomechanics that can in turn cause or exacerbate co-existing spinal instabilities and degeneration at other spinal levels or in other joints associated with spinal motion.

There is a cause-and-effect relationship among intervertebral disc integrity, facet loads, and spinal degeneration. Specifically, the progressive loss of disc height with disc degeneration often also alters the facet joint's mechanical ability as the facet joints degenerate or dislocate, and ligaments lose elasticity and their load-carrying ability. More specifically, with disc-space narrowing, as frequently occurs with degenerative disc disease, there is an increased load in the facet joints, especially in extension, and concomitant degeneration of the facet joints and capsules.

Since the facet joint capsules are primarily loaded in flexion and in rotation, and the facet joints are the primary resistors against rotational or torsional forces (e.g., normally, the facet joints control approximately 30% of axial rotation), facet joint degeneration significantly alters spinal mobility.

The need to provide minimally invasive therapies that provide pain relief while restoring and preserving the biomechanical function of the physiological facet joints is paramount to overall spinal mobility, and to date, therapies have not adequately satisfied all of these issues, as noted below.

One therapy, facet rhizotomy, involves techniques that sever small nerves that go to the facet joint. The intent of the procedure is to stop the transmission of pain impulses along these nerves. The nerve(s) is identified using a diagnostic injection. Then, the surgeon inserts a large, hollow needle through the tissues in the low back. A radiofrequency probe is inserted through the needle, and a fluoroscope is used to guide the probe toward the nerve. The probe is slowly heated until the nerve is severed.

Another technique using pulsed radiofrequency does not actually burn the nerve, rather it is believed to stun the nerve. Yet another technique involves denervation by probe tip freezing, and still another procedure involves carefully controlled injection of botox toxin to treat muscle spasm, a protective reflex that may occur when the facets are inflamed that in turn causes the nearby muscles that parallel the spine to go into spasm.

While these procedures may provide pain relief, they do not address ongoing joint degeneration (e.g., wear on articulating surfaces), which leads to kinematic and biomechanical dysfunction that may in turn lead to transition syndrome (i.e., progression of degeneration and pain to other joints) at other levels.

While certain clinicians have advocated prosthetic total joint replacement of damaged facet joints, in practice, it is difficult to implement such a prosthesis for a variety of reasons including the variability of facet joint geometry from facet joint to facet joint, and the high level of interaction between the facet joint and the other components in the spinal column.

Moreover, joint replacement is a highly invasive and time-consuming procedure, requiring pre-preparation of joint surfaces and removal of bone, and thus there are associated risks, including blood loss and morbidity, increased anesthesia time, and increased convalescence time.

A related therapeutic treatment of the facet joint entails the provision of an artificial facet joint where the inferior facet segment, the mating superior facet segment, or both, are covered with a cap (i.e., over all, or substantially all, of the facet). One such device and related method of implantation is described in Fitz, U.S. Pat. No. Re 36,758.

While potentially viable, the capping of the facet segments has several potential disadvantages. Clinical concerns are believed to result from the disruption of the periosteum and ligamentum teres femoris, both serving a nutrition delivery role to the femoral head, thereby leading to avascular necrosis of the bony support structure for the cap.

Another potential disadvantage of facet capping is that to accommodate the wide variability in anatomical morphology of the facets, not only between individuals, but also between levels within the spinal column, a very wide range of cap sizes and shapes is required.

Even further, implantation of the caps, such as those described in U.S. Pat. No. Re 36,758, cannot be performed on a minimally-invasive basis, and entail fairly significant preparatory steps at the implantation site (e.g., removal and/or re-shaping of bone). At least with use of caps over osteoarthritic femoral heads, the capping of articular bone ends has sometimes experienced clinical failure by mechanical loosening.

Another therapeutic treatment of the facet joint is to affix the superior articular process to the inferior articular process using a facet screw. Although the fixation therapy may alleviate symptoms associated with a degenerated facet joint, it also sacrifices some of the ability of the motion segment to move and thus sacrifices some of the ability of the spinal column to move in a natural manner.

Central and lateral spinal stenosis (joint narrowing), degenerative spondylolisthesis, and degenerative scoliosis may all result from the abnormal mechanical relationship between the anterior and posterior column structures and induce debilitating pain. More recently, a percutaneouslyimplantable, facet joint stabilization device has been developed, and is described in U.S. application Ser. No. 12/238, 196 (filed Sep. 25, 2008 and entitled "Method and Apparatus for Facet Joint Stabilization"), the teaching of which are incorporated herein by reference. The facet joint stabilization device generally entails a superior body and an inferior body that, when combined, form an exteriorly threaded device.

When inserted into the joint space, the inferior and superior bodies establish an engaged relationship with the corresponding inferior and superior bony faces of the facet joint anatomy, respectively, and are somewhat slidable relative to one another to facilitate near normal facet joint motion ability. While viable, areas for improvement remain, including retention, long-term functioning, and insertion techniques.

As the present disclosure contemplates accessing various vertebral elements and joints through a preferred approach that comes in from a percutaneous posterior approach, "proximal" and "distal" are defined in context of this channel of approach. Consequently, "proximal" is closer to the beginning of the channel and thus closer to the clinician, and "distal" is further from the beginning of the channel and thus more distant from the clinician.

When referencing access or delivery tools, "distal" would be the end intended for insertion into the access channel, and "proximal" refers to the opposing end, generally the end closer to the handle of the delivery tool. When referencing implants, generally "distal" would be the leading end first inserted into the joint and "proximal" refers to the trailing end, generally in an engagement with a deployment tool.

In light of the above, a need exists for additional therapies applicable to facet joints to stabilize and augment the facet joint in alleviating problems without initial resort to the more radical therapies of replacing the facet joint with a prosthesis and/or fixation of the facet joint and the inherent loss of natural movement of that motion segment.

SUMMARY OF THE INVENTION

An embodiment of the invention is directed to a method of resurfacing a facet joint with a facet implant system. The facet joint has a superior facet and an inferior facet that are adjacent to each other and movable with respect to each other.

A first facet implant component is provided that has a first visualization marker. The first visualization marker includes a first marker section and a second marker section. The first marker section is oriented at an angle with respect to the second marker section.

The first facet implant component is implanted between the superior facet and the inferior facet. A location and an orientation of the first facet implant component are determined using an imaging technique that locates the first visualization marker.

Another embodiment is directed to a method of resurfacing a facet joint with a facet implant system. The facet joint has a superior facet and an inferior facet that are adjacent to each other and movable with respect to each other.

A first facet implant component is provided that has a first visualization marker. The first visualization marker includes a first marker section and a second marker section. The first marker section is oriented at an angle with respect to the second marker section.

A second facet implant component is provided that has a second visualization marker with respect to the second articulating surface. The second visualization marker includes a third marker section and a fourth marker section. The third marker section is oriented at an angle with respect to the fourth marker section.

The first facet implant component and the second implant component are implanted between the superior facet and the inferior facet so that the first facet implant component is adjacent to the second implant component. A location and an orientation of the first facet implant component and the second facet implant component are determined using an imaging technique that locates the first visualization marker and the second visualization marker.

Another embodiment is directed to a method of resurfacing a facet joint with a facet implant system. The facet joint has a superior facet and an inferior facet that are adjacent to each other and movable with respect to each other.

A first facet implant component is provided that has a first visualization marker. The first visualization marker includes a first marker section and a second marker section. The first marker section is oriented at an angle with respect to the second marker section.

A second facet implant component is provided that has a second visualization marker. The second visualization marker includes a third marker section and a fourth marker section. The third marker section is oriented at an angle with respect to the fourth marker section;

The first facet implant component and the second implant component are implanted between the superior facet and the inferior facet so that the first facet implant component is adjacent to the second implant component, at least a portion of the first marker section overlaps the third market section and at least a portion of the second marker section does not overlap the fourth marker section.

A location and an orientation of the first facet implant component and the second facet implant component is determined using an imaging technique that locates the first visualization marker and the second visualization marker.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 20 is a side view of a delivery cannula according to an embodiment of the invention.

FIG. 21 is a side view of an implant insertion tool according to an embodiment of the invention.

FIG. 22 is a side view of an implant insertion tool according to an alternative embodiment of the invention.

DETAILED DESCRIPTION OF THE PREFERRED EMBODIMENTS

Figure 2:
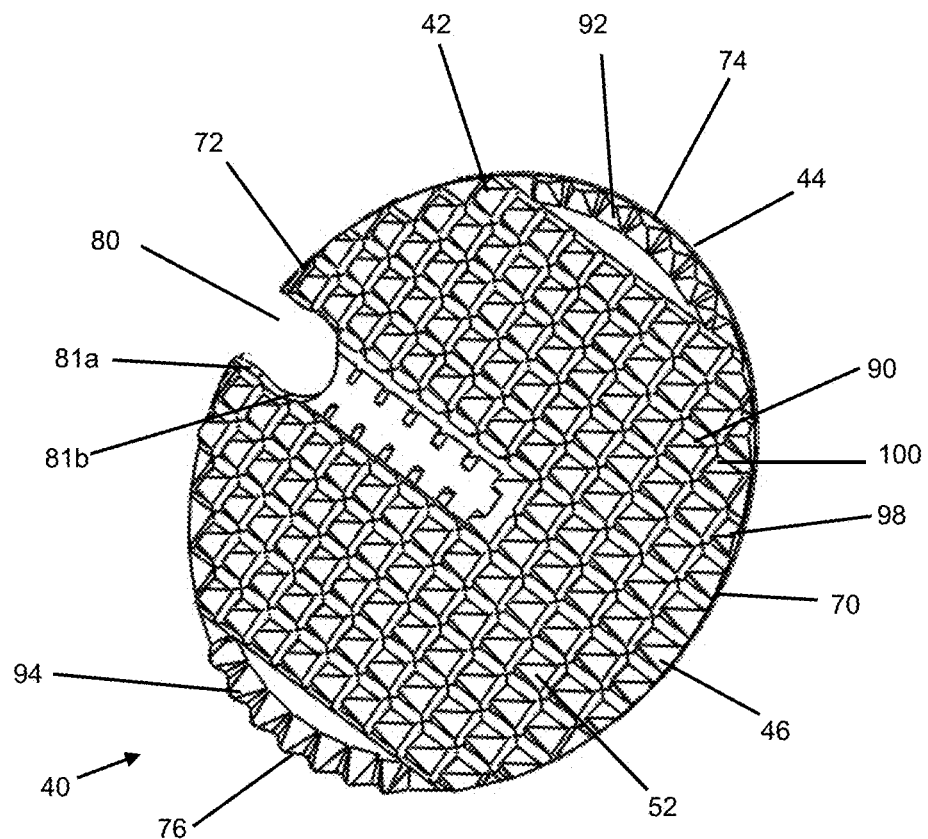
FIG. 2 is a perspective view of a resurfacing body according to an embodiment of the invention.

One embodiment of an implant system 40 in accordance with principles of the invention and useful for treating a facet joint of a patient is illustrated in FIG. 2. The implant system 40 may include a superior resurfacing device 42 and an inferior resurfacing device 44.

As illustrated in FIG. 2, the superior resurfacing device 42 may be positioned on top of the inferior resurfacing device 44 so that the superior resurfacing device 42 and the interior resurfacing device 44 are oriented in opposite directions as the superior resurfacing device 42 and the inferior resurfacing device 44 would be oriented during the implantation process. Details on the various components of the resurfacing devices 42, 44 are provided below.

Figure 1:
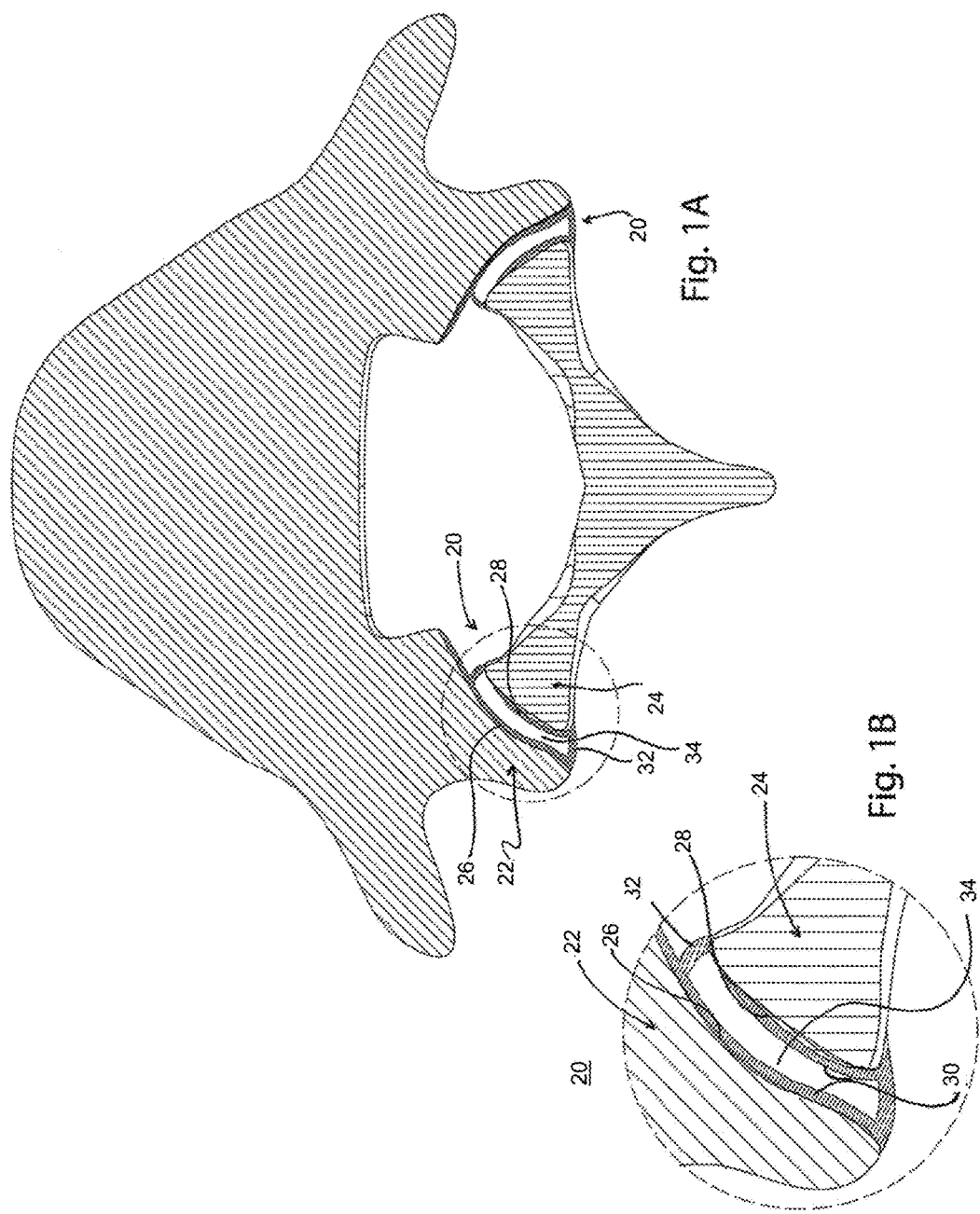
FIG. 1A is a simplified cross-sectional view of a human spinal segment illustrating anatomy of native facet joints with which the systems and methods of the present disclosure are useful in treating.
FIG. 1B is an enlarged view of one facet joint of the segment of FIG. 1A.

In certain embodiments, the resurfacing devices 42, 44 may be substantially similar to each other where the superior resurfacing device 42 is placed adjacent to a superior facet joint articular face (e.g., the superior articular face 26 of FIG. 1B), and the inferior resurfacing device 44 is placed adjacent to an inferior facet joint articular face (e.g., the inferior articular face 28 of FIG. 1B).

The resurfacing devices 42, 44 may be capable of substantially conforming to the naturally-occurring shape or curvature of the facet joint anatomy. The resurfacing devices 42, 44 thereby replace the bone-on-bone interface of the natural facet joint in a manner achieving normal or near normal mobility.

While not required, the resurfacing devices 42, 44 may be substantially similar to each other in some embodiments. As such, the following description of the superior resurfacing device 42 is equally applicable to the inferior resurfacing device 44.

The resurfacing device 42 consists of a resurfacing body 46. In certain embodiments described below, one or more additional components can be attached to, or extend from, the resurfacing body 46. In certain embodiments, the resurfacing body 46 may have a disc-like shape, that includes a base web 50 and a plurality of teeth 52 (referenced generally).

Figure 3:
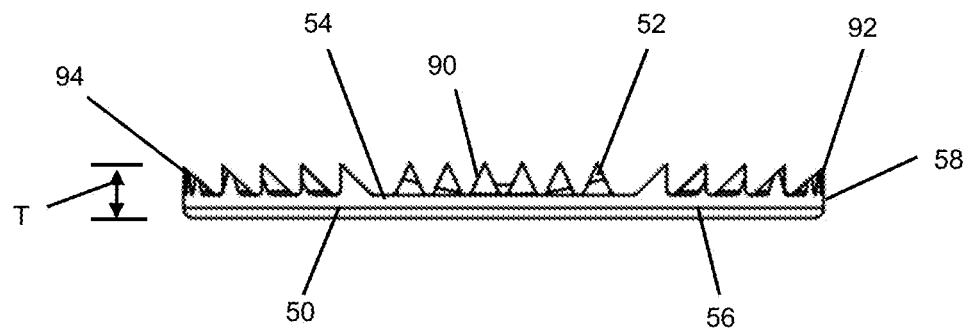
FIG. 3 is a side view of the resurfacing body of FIG. 2.

The base web 50 defines opposing major surfaces 54, 56, as illustrated in FIG. 3, with the first major surface 54 providing or serving as an articulating surface (e.g., articulates relative to a corresponding articulating surface of the inferior resurfacing device 44 (FIG. 2)) as described below. Thus, the first major surface 54 may also be referenced as the "articulating surface" of the resurfacing body 46. The plurality of teeth 52 may project from the second major surface 56 in a direction that is generally opposite the first major surface 54.

With specific reference to FIGS. 2 and 3, the base web 50 defines an outer perimeter 58 of the resurfacing body 46. In certain embodiments, the outer perimeter 58 may have a generally circular shape that generally conforms to a shape of the facet joint in which the resurfacing body is to be implanted. In other embodiments, the perimeter may have an oval-like shape (relative to a top or bottom plan view). The resurfacing device 44 may be formed with other shapes, examples of which include square, rectangular, hexagonal and curvilinear.

An overall size or footprint of the resurfacing body 46 is defined by the outer perimeter 58 and can vary depending upon a size of the facet joint being treated, but is generally relatively small, especially as compared to conventional facet joint prostheses and/or capping devices. As is noted above, the resurfacing body 46 should be large enough to prevent bone-to-bone contact in the facet joint.

In certain embodiments, a diameter of the resurfacing body 46 may be in the range of between about 3 millimeters and about 15 millimeters. In other embodiments, the diameter of the resurfacing body may be in the range of between about 5 millimeters and about 10 millimeters.

Facet joint treatment systems in accordance with this invention may be provided to a treating clinician with two or more different superior resurfacing devices 42 (and two or more different inferior resurfacing devices 44) each having a differently-sized resurfacing body 46.

Examples of the sizes of the resurfacing bodies include about 5 millimeters, about 8 millimeters, about 10 millimeters and about 12 millimeters. The treating clinician may select the most appropriately sized resurfacing device for implantation based upon an evaluation of the facet joint to be treated.

While it is desirable for the resurfacing body 46 to be sufficiently large to prevent bone-to-bone contact within the facet joint, the resurfacing body 46 should not be too large such that the resurfacing body 46 extends beyond the facet joint as such a condition could result in damage to the tissue adjacent to the facet joint where the resurfacing body 46 is implanted.

For reasons that are set forth in more detail below, the resurfacing body 46 may incorporate one or more features dictating a preferred insertion orientation and/or direction. For example, the resurfacing body 46 may be more readily inserted into, and subsequently retained within, a facet joint in a particular orientation.

Relative to the configuration of FIGS. 2 and 3, the outer perimeter 58 can be described as generally defining a leading or distal end 70, a trailing or proximal end 72, and opposing sides 74, 76. During an insertion procedure, the resurfacing body 46 may be oriented such that the leading end 70 is initially inserted into the facet joint, followed by the trailing end 72.

In addition to the teeth 52 having a structure corresponding with these designations (and thus the intended insertion direction and orientation described below), the trailing end 72 can form or define an engagement feature 80, as illustrated in FIG. 2, that promotes desired interaction with a separately-provided insertion tool, which is discussed in more detail below.

In certain embodiments, the engagement feature 80 is an aperture that includes at least two aperture regions 81a, 81b. The first aperture region 81a may intersect the outer perimeter 58 or edge proximate the trailing end 72. The second aperture region 81b is in communication with the first aperture region 81a and is oriented on a side of the first aperture region 81a that is opposite the outer perimeter 58.

The first aperture region 81a may have a width that is smaller than a width of the second aperture region 81b. The shape of the engagement feature 80 thereby provides a partially enclosed aperture to facilitate attachment of the resurfacing body 46 to the implant insertion tool during the insertion process.

A force to separate the resurfacing body 46 from the implant insertion tool should be sufficiently large so that the resurfacing body 46 does not inadvertently separate from the implant insertion tool 312. In certain embodiments, the force to separate the resurfacing body 46 from the implant insertion tool 312 is at least 1 Newton. In other embodiments, the force to separate the resurfacing body 46 from the implant insertion tool 312 is between about 1 Newton and about 10 Newtons. In still other embodiments, the separation force is about 5 Newtons.

The separation force may be affected by a difference in the sizes of the widths of the first aperture region 81a and the second aperture region 81b and the width of the extension. The separation force may also be affected by other factors such as the rigidity of the resurfacing body 46 and the extension on the implant insertion tool 312. For example, if the resurfacing body 46 or the extension is fabricated from a flexible material, the separation force may be lower if the resurfacing body 46 or the extension is fabricated from a relatively rigid material.

The engagement feature 80 may be formed at the same time the other portions of the resurfacing body 46 are formed such as by molding. Alternatively, the engagement feature 80 may be formed after the resurfacing body 46 is formed such as by stamping out the region that defines the first aperture region 81a and the second aperture region 81b.

It is possible to use other techniques for maintaining the resurfacing device 46 in engagement with the implant insertion tool 312 during the process of inserting the resurfacing device 46 into the facet joint. An example of one such alternative attachment technique is attaching the resurfacing device 46 and the implant insertion tool 312 with a frangible connection. When a force that is greater than a threshold force, the frangible connection may be severed to thereby allow the implant insertion tool 312 to be removed while leaving the resurfacing body 46 in the facet joint. In certain embodiments, the force to sever the frangible connection is at least 1 Newton. In other embodiments, the force to sever the frangible connection is between about 1 Newton and about 10 Newtons. In still other embodiments, the separation force is about 5 Newtons.

In certain embodiments, the base web 50 has, in some constructions, a relatively uniform thickness (e.g., nominal thickness variation of +/−0.05 mm), as illustrated in FIG. 3. The base web 50 forms the articulating surface 54 to be relatively smooth. This smoothness attribute is, at least in part, a function of the material employed for the resurfacing body 46 as described below.

In other embodiments, the articulating surface 54 of the base web 50 may be coated with a separate layer that provides enhanced frictional (i.e., lower coefficient of friction) and wear characteristics. An example of one such material have a low coefficient of friction is polytetrafluoroethylene (PTFE), which is available under the designation TEFLON.

The plurality of teeth 52 project from the second major surface 56 of the base web 50. These teeth 52 may have a variety of forms. In some embodiments, the teeth 52 are arranged to form or define discrete zones or teeth sets, such as the first, second and third teeth sets 90, 92, 94 generally identified in FIG. 2.

The first teeth set 90 may be centrally located along the base web 50 extending between the leading and trailing ends 70, 72. Individual teeth of the first teeth set 90 may be generally identical. More particularly, each of the teeth may include a leading face 98 and a trailing face 100 that extends from the second major surface 56 and intersect at a tip 102. The leading face 98 may be oriented more proximate the leading end 70 (as compared to the trailing face 100), whereas the trailing face 100 may be oriented more proximate the trailing end 72.

With these designations in mind, the teeth may be constructed to define an insertion direction whereby an angle α formed by the leading face 98 relative to the second major surface 56 is smaller than an angle β formed by the trailing face 100 relative to the second major surface 56.

In these configurations, the leading face 98 may have a more gradual slope relative to the leading end 70 as compared to a slope of the trailing face 100 relative to the trailing end 72 such that the tooth 96a more overtly engages a separate structure, such as the facet joint superior face (not shown) at and along the trailing face 100 as compared to the leading face 98.

In some configurations, the angle α defined by the leading face 98 may be in the range of 20°-60°, whereas the angle β defined by the trailing face 100 is approximately 90°. Suitable angles may be affected by a variety of factors such as the material from which the resurfacing body 46 is fabricated. Regardless, and returning to FIG. 2, the remaining teeth of the first teeth set 90 may be aligned with one another in two or more rows as shown.

The second teeth set 92 and the third teeth set 94 may be formed at or along the opposing sides 74, 76, respectively, as illustrated in FIG. 2. In this regard, while the individual teeth of the second and third sets 92, 94 may have the non-symmetrical relationship described above with respect to the tooth discussed above, an exterior face 103 associated with each tooth of the second and third teeth sets 92, 94 establish an angle of extension relative to the second major surface 56 that approaches 90°.

With this but one acceptable construction, the second and third teeth sets 92, 94 overtly resist side-to-side displacement of the resurfacing body 46 relative to a corresponding facet joint face following insertion. For example, the second teeth set 92 may resist leftward displacement of the resurfacing body 46, whereas the third teeth set 94 may resist rightward displacement.

In certain embodiments, each tooth of the plurality of teeth 52 may have an identical, or nearly identical, height (or extension from the second major surface 56), as illustrated in FIG. 3. In other embodiments, the teeth of the first teeth set 90 may have an elevated height as compared to teeth of the second and third teeth sets 92, 94, and combine to define a tapering height of the resurfacing body 46 from the leading end 70 to the trailing end 72.

Stated otherwise, and relative to the illustrated embodiment in which the first major surface 54 is planar, a height of the leading tooth 96a is greater than a height of a trailing tooth 96b. For example, the tips 102 associated with the teeth of the first teeth set 90 combine to define a hypothetical plane P. The plane P is, in some embodiments, non-perpendicular relative to a plane of the first major surface 54, combining with the first major surface 54 to define an included angle Δ in the range of between about 1° and about 5°.

In other embodiment, other angles are also contemplated where the teeth 52 have substantially similar heights. In certain embodiments, the tallest tooth 96a may be provided at the leading end 70 that ultimately is located opposite the point of insertion into the facet joint. As a result, the leading tooth 96a may establish a more rigid engagement with the corresponding facet joint face to thereby overtly resist displacement upon final insertion.

The base web 50 and the teeth 52 combine to define an overall thickness T of the resurfacing body 46. For example, a lateral distance between the first major surface 54 and the tip 102 of the "tallest" tooth 96a. As described in greater detail below, a desired conformability characteristic of the resurfacing body 46 is influenced by the overall thickness T and the base web thickness t, and thus the overall thickness T is selected, along with other parameters, to effectuate the desired degree of conformability.

In some constructions, the overall thickness T of the resurfacing body 46 is between about 0.25 millimeters and about 4 millimeters, although other dimensions are also contemplated. As a point of reference, the overall thickness T associated with the resurfacing body 46 selected by the treating clinician for insertion into a particular facet joint may vary as a function of other procedures associated with the insertion.

For example, where the resurfacing body 46 is inserted into a facet joint without any overt tissue removal prior to insertion, the overall thickness T can be between about 0.5 millimeters and about 2.5 millimeters. If the insertion procedure entails first removing cartilage (or other tissue) from the facet joint, a larger version of the resurfacing body 46 can be inserted, such that the overall thickness T of the resurfacing body 46 is between about 0.5 millimeters and about 3 millimeters.

The resurfacing devices 42, 44, and thus the corresponding resurfacing bodies 46, may be integrally formed of a robust material that achieves desired conformability. The resurfacing body 46 in accordance with this invention maintains its structural integrity (i.e., little or no wear) without adhesive or cohesive damage when subjected to typical articulation of the facet joint with movement of the patient.

In some constructions, the resurfacing devices 42, 44 may be formed of an implantable-grade plastic, although other materials such as metal are also available. For example, the resurfacing devices 42, 44 may be made from the polyetherketone (PEK) family of plastics, which have strength, wear, flexibility, and biocompatibility properties appropriate for insertion into, and long-term functioning within, the facet joint.

Polyetheretherketone (PEEK) has been found to provide not only the conformability attributes described below, but also long-term mechanical strength and resistance to wear. Additional materials may be incorporated, such as those exhibiting radio-opacity properties. For example, the resurfacing devices 42, 44 may be formed from a radio-opaque mineral (e.g., barium)-loaded PEK composition.

Figures 4, 5:
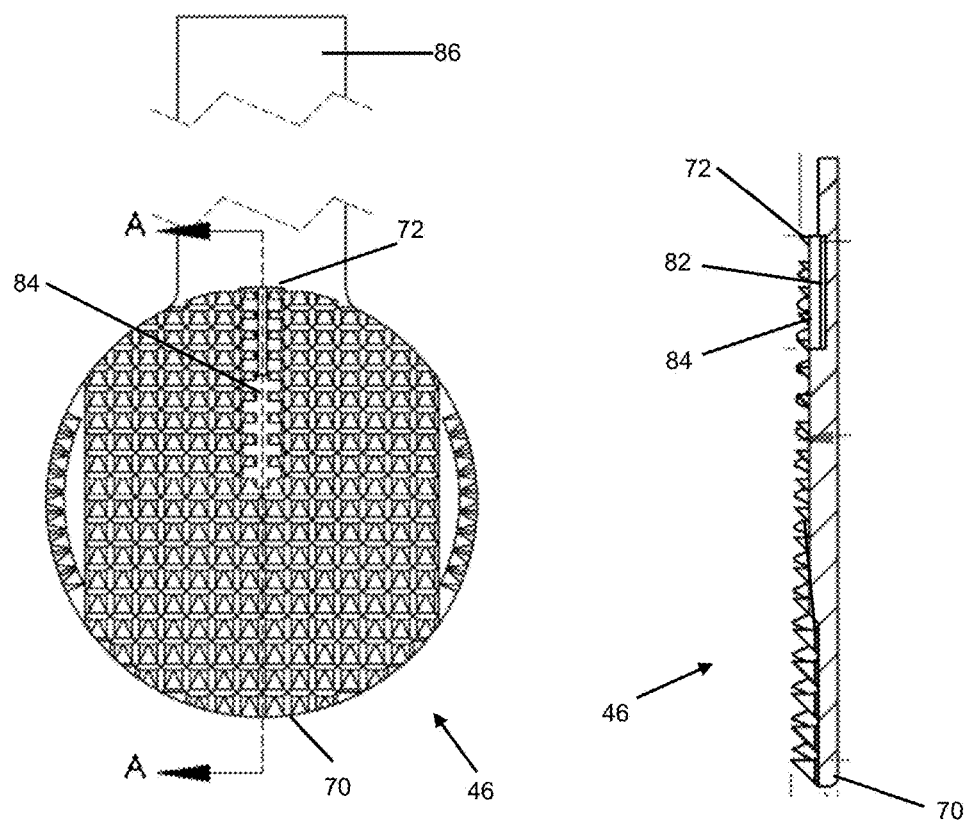
FIG. 4 is top view of another configuration of the resurfacing body having a tab extending therefrom.
FIG. 5 is a sectional view of the resurfacing body taken along a line A-A in FIG. 4.

Visualization may also be provided via one or more radio-opaque marker bands (e.g., platinum marker band). The marker band(s) can be embedded within the resurfacing device 42, 44. For example, a radio-opaque rod may be inserted into a hole formed in the resurfacing device 42, 44, as illustrated in FIG. 5. Alternatively, the radio-opaque material may be inserted around a perimeter of the resurfacing device 42, 44.

The selected materials, shapes, and dimensions associated with the resurfacing body 46 of each of the resurfacing devices 42, 44 impart or create a conformability property to the resurfacing body 46 sufficient to allow the resurfacing body 46 to "match" the multi-planar concavity associated with a native facet joint articular face anatomy.

With the resurfacing device 42, 44 embodiment of FIG. 2, the resurfacing body 46 forms an entirety of the corresponding resurfacing device 42, 44. In other embodiments described below, one or more additional components may be included with the resurfacing body 46, such that the following explanation of conformability is specifically applicable to the resurfacing body 46, but may also apply equally to the resurfacing devices 42, 44 as a whole.

In general terms, "conformability" may be inversely proportional to bending stiffness of the resurfacing body 46 during insertion, and may be increased as the resurfacing body 46 heats to body temperature and is allowed to creep. From a clinical perspective, "conformability" of the resurfacing body 46 entails the resurfacing body 46 conforming to a radius of curvature of the C-shaped or J-shaped portions of the articular joint such as the concave-shaped superior articular face 26 of FIG. 1B or the convex-shaped inferior articular face 28 of FIG. 1B.

As a point of reference, the minimum radius of curvature of the human facet joint in the transverse plane is on the order of 20 millimeters, with a lower bound (10th percentile) on the order of 7 millimeters. The radius of curvature will vary with the vertebral level and the patient's specific anatomy and disease state. Preparation of the facet joint prior to insertion of the resurfacing devices 42, 44 may also change the radius of curvature.

A range of curvature radii of 7 millimeters to infinity (i.e., flat facet anatomy) can be accommodated by the resurfacing devices 42, 44 of the present disclosure. There also may be curvature in the sagittal plane; the conformable nature of the resurfacing body 46 of the present disclosure is capable of substantially "matching" any sagittal plane curvature as well.

With the above understandings in mind, the conformability characteristic of the resurfacing body 46 is sufficient such that the resurfacing body 46 readily transition from the relatively flat state illustrated in FIG. 2 to an inserted state (not shown but reflected, for example, in FIG. 30) in which the resurfacing body 46 substantially matches or mimics the naturally-occurring shape (e.g., radius of curvature of curved portions) of the facet joint face to which the resurfacing body 46 is secured. In this regard, the facet joint 20 (FIG. 1B) is subject to, or experiences, various loads that effectuate compressive forces at the region of interface between the superior and inferior articular faces 26, 28 (FIG. 1B).

These physiologic forces across the facet joint 20 will vary with activity, posture, body loads, and muscle forces, and tend to be between about 7% and about 14% of body load when standing. However, in the prone, slightly flexed position during surgery/implantation, these loads may be as little as zero. The intrinsic forces will be generated as the resurfacing device 42, 44 (and thus the corresponding resurfacing body 46) are inserted and the capsule 32 (FIG. 1B) is tensioned. Compression of the underlying cartilage and subchondral bone, slight flexion, or laminar strains may result and would accommodate some thickness of the devices 42, 44. However, separation/posterior translation of the superior facets would be required to accommodate a large portion of a collective thickness of the devices 42, 44.

Compressive loads normal to and across the articular faces 26, 28 will be generated upon separation/posterior translation of the superior facets due to joint capsule tensioning. The conformable nature of the resurfacing body 46 is such that in the presence of these typical compressive forces, the resurfacing body 46 will transition from the relatively flat state to the inserted state in which the resurfacing body 46 substantially matches the geometry of the facet joint surface to which the resurfacing body 46 is secured.

For example, the resurfacing body 46 will flex to conform with a macroscopic shape/contour of the native articular face to which the resurfacing body 46 is applied, but may not conform to the microscopic variations in the native articular face because of small deviations due to cartilage defects, bony fissures, or small voids during preparation of the joint (typically between about 0.05 millimeters and about 0.5 millimeters in width).

This process will occur as the compressive forces applied by the ends of the hypothetical concave region of one facet articular surface (e.g., the superior articular surface 26) and the center of the corresponding convex surface on the opposing articular facet (e.g., the inferior articular surface 28) generate a bending moment on the resurfacing body 46 that produces strain to conform the resurfacing body 46 to the native anatomy.

As used through this specification, a resurfacing body that conforms to the minimum radius of curvature of an adult human facet joint under normal physiologic forces (e.g., between about 180 and about 450 Newtons/millimeter per segment assuming a net 1 millimeter posterior shear translation) without deviations from the articular surface to which the resurfacing body is applied of greater than 1 millimeter is defined as being "conformable" and "substantially matching" the multi-planar curvatures of a facet joint.

Alternatively, a resurfacing body sized for placement within an adult human facet joint and exhibiting a Conformability Factor (described below) of not more than 100 Newtons is also defined as being "conformable" and "substantially matching" the multi-planar curvatures of a facet joint in accordance with the present disclosure. In some embodiments, resurfacing bodies in accordance with the present disclosure exhibit a Conformability Factor of not more than 50 Newtons, and in other embodiments not more than 25 Newtons.

It has surprisingly been found that forming the resurfacing body 46 (and thus either of the resurfacing devices 42, 44 of the one embodiment of FIG. 2) of PEEK and with the footprint size and thickness dimensions described above achieves the desired conformability characteristics, long-term resistance to wear, and facet joint stabilization following insertion.

Figure 6:
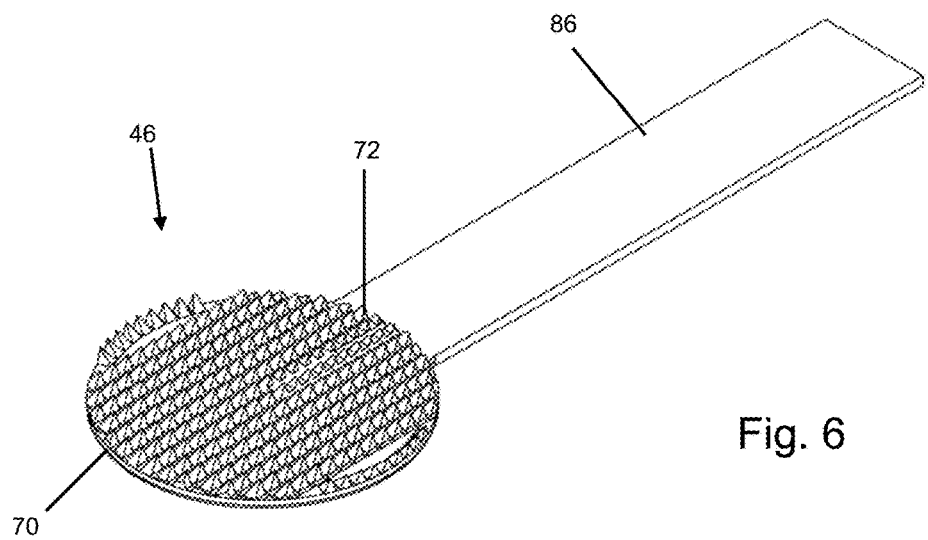
FIG. 6 is a perspective view of the resurfacing body of FIG. 4.

Another embodiment of the resurfacing body 46 is illustrated in FIGS. 4-6. The resurfacing body 46 may have a similar over shape and a similar tooth pattern to the resurfacing body illustrated in FIGS. 2-3 except as noted below.

The resurfacing body 46 may include a radio opaque marker 82 placed therein. The radio opaque marker 82 may be utilized to monitor the location of the resurfacing body 46 is implanted in a non-invasive manner as the radio opaque marker 82 may be viewed using many different types of imaging conventionally used in the medical field.

The radio opaque marker 82 should be sufficiently large to facilitate viewing the radio opaque marker using conventional medical imaging techniques. However, the radio opaque marker 82 should be sufficiently small such that the radio opaque marker 82 does not impede the flexibility of the resurfacing body 46 after implantation. Alternatively or additionally, the radio opaque marker 82 may be fabricated from a flexible material that does not impede the ability of the resurfacing body 46 to flex after implantation.

While it is possible to incorporate the radio opaque marker 82 during the process used to fabricate the resurfacing body 46, it is also possible to insert the radio opaque marker 82 into the resurfacing body 46 after fabrication.

One such suitable technique for inserting the radio opaque marker 82 into the resurfacing device includes forming an aperture in the resurfacing body 46. In certain embodiments, the aperture may be formed using a drill.

In certain embodiments, the radio opaque marker 82 may be placed into the resurfacing body 46 from a trailing end 72 thereof proximate a center line of the resurfacing body 46. Using such a configuration provides the resurfacing body 46 with symmetry to assist in evaluating the position of the resurfacing body 46 based upon medical imaging of the radio opaque marker 82.

The placement of the radio opaque marker 82 in the resurfacing body 46 should be relatively accurate such that the radio opaque marker 82 does not extend through one of the surfaces of the resurfacing body 46. Such an occurrence could lead to degradation of the resurfacing body 46 or could cause damage to the tissue in the facet joint that is adjacent to the resurfacing body 46.

To ensure that the radio opaque marker 82 does not extend through the upper surface of the resurfacing body 46, an additional material region 84 may be provided in the region adjacent to the radio opaque marker 82, as illustrated in FIGS. 4 and 5. The radio opaque marker 82 may be placed at an approximately equal distance between the upper and lower surfaces of the resurfacing body in the additional material region 84.

An elongated tab 86 may extend from the trailing end 72 of the resurfacing body 46. The elongated tab 86 could be used in the manufacturing process and then be severed from the other portions of the resurfacing body 46 once manufacturing is completed. Alternatively, the elongated tab 86 may be used in conjunction with the insertion of the resurfacing body 46 into the facet joint as opposed to the implantation system described herein. In such instances, a line of weakening may be provided where the elongated tab 84 intersects the resurfacing body 46.

Figures 7, 8:
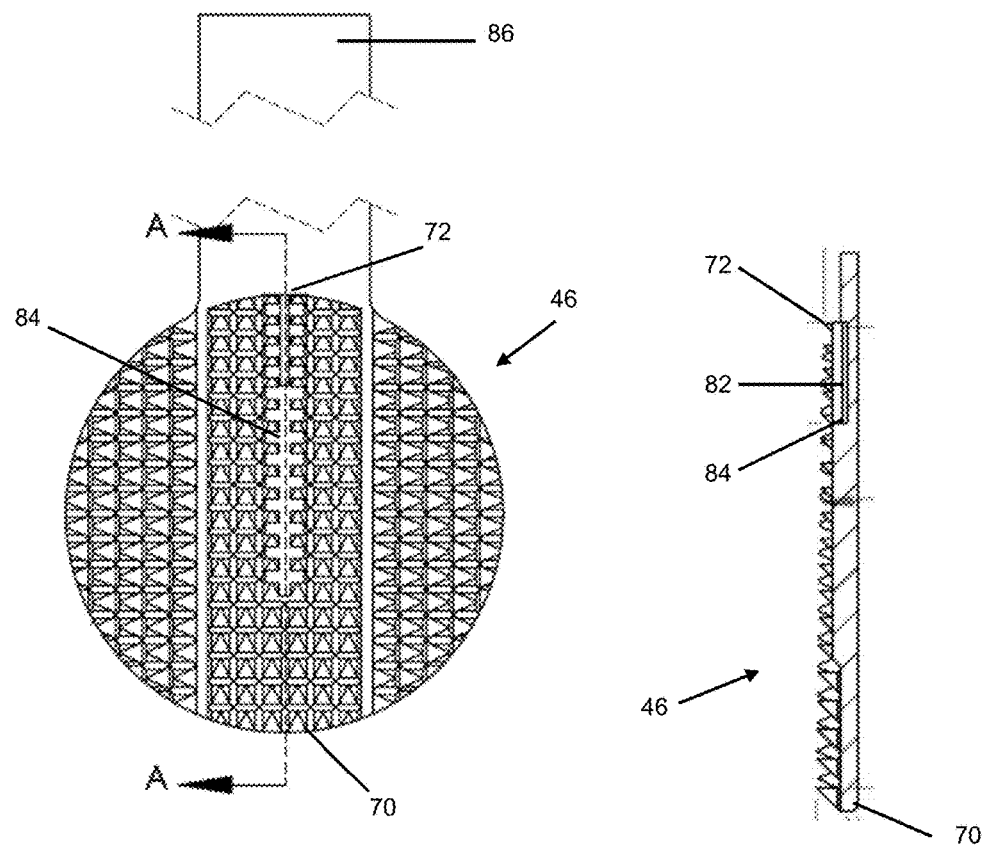
FIG. 7 is a top view of another configuration of the resurfacing body having a tab extending therefrom.
FIG. 8 is a sectional view of the resurfacing body taken along a line A-A in FIG. 7.
Figure 9:
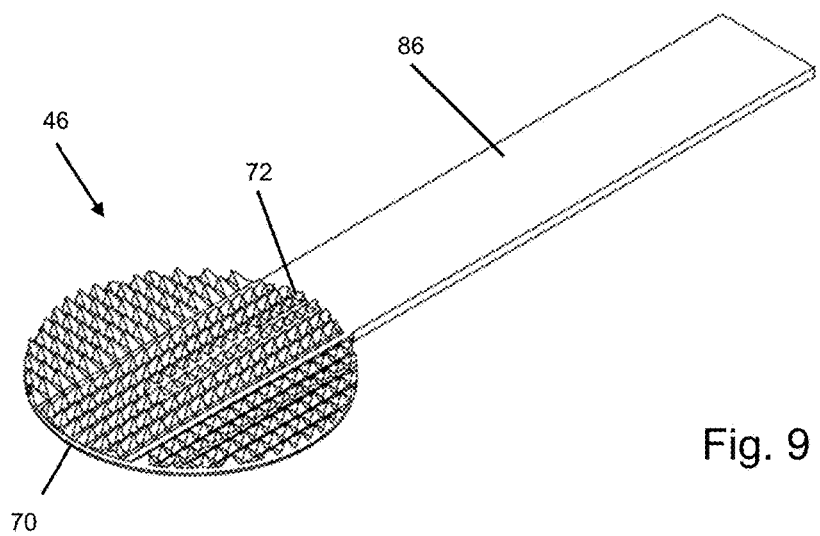
FIG. 9 is a perspective view of the resurfacing body of FIG. 7.

Another embodiment of the resurfacing body 46 is illustrated in FIGS. 7-9. The resurfacing body 46 may have a similar over shape and a similar tooth pattern to the resurfacing body illustrated in FIGS. 2-3 except as noted below.

The resurfacing body 46 may include a radio opaque marker 82 placed therein. The radio opaque marker 82 may be utilized to monitor the location of the resurfacing body 46 is implanted in a non-invasive manner as the radio opaque marker 82 may be viewed using many different types of imaging conventionally used in the medical field. The features and placement of the radio opaque marker 82 are similar to the features and placement of the radio opaque marker 82 in the embodiment of the resurfacing body 46 illustrated in FIGS. 4-6

An elongated tab 86 may extend from the trailing end 72 of the resurfacing body 46. The structure and function of the elongated tab 86 may be to the structure and function of the elongated tab 86 in the embodiment of the resurfacing body 46 illustrated in FIGS. 4-6.

The resurfacing body 46, and thus the system 40, may be delivered to, and inserted within, a facet joint in a variety of manners via various instrumentations sets or systems. Components of one useful insertion tooling set are discussed below.

One of the important aspects of accurately delivering the resurfacing body 46 is to not only accurately locate the desired facet joint but also to accurately position the resurfacing body delivery system with respect to the facet joint to permit the resurfacing body 46 to be accurately inserted into the facet joint.

Figure 10:
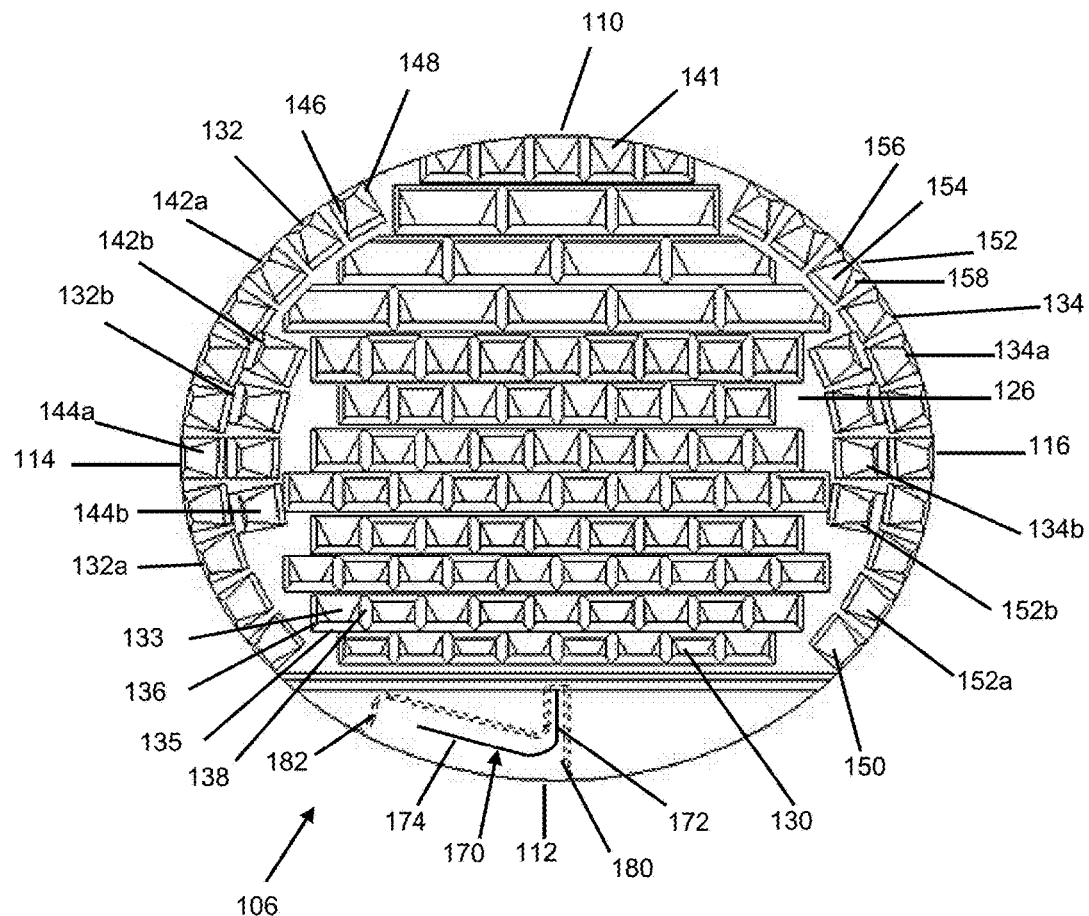
FIG. 10 is a top view of an alternative embodiment of the implant.
Figure 11:
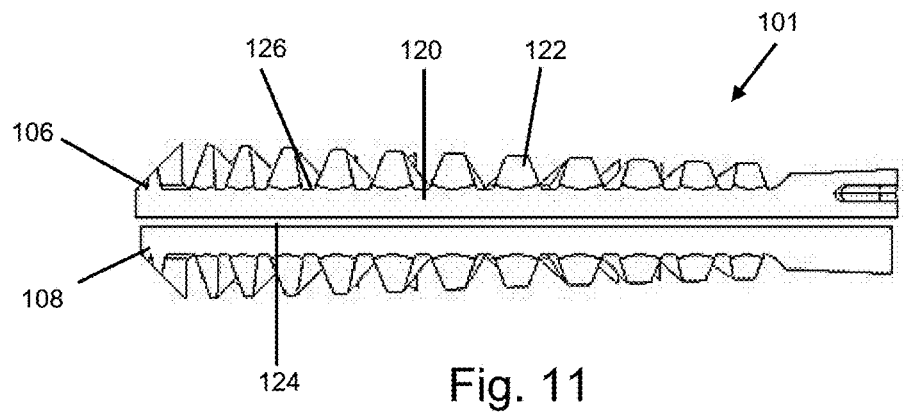
FIG. 11 is a side view of two of the implants of FIG. 10 positioned in an insertion orientation.

Another embodiment of the invention is directed to an implant system 101, as illustrated in FIGS. 10-13. In certain embodiments, the implant system 101 includes a superior resurfacing device 106 and an inferior resurfacing device 108, as illustrated in FIG. 11.

The superior resurfacing device 106 serves as a liner for a superior facet and the inferior resurfacing device 108 serves as a liner for an inferior facet. In certain embodiments, the resurfacing devices 106, 108 are capable of conforming to the naturally-occurring shape or curvature of the facet joint anatomy.

The resurfacing devices 106, 108 thereby replace a bone-on-bone interface caused by degradation of the natural joint in a manner achieving normal or near normal mobility of the vertebrae. It is also possible to use the concepts of the invention in conjunction with other articular joints.

The superior resurfacing device 106 and the inferior resurfacing device 108 may each have a substantially similar shape. As such, the description herein is provided with respect to the superior resurfacing device 106.

Figure 12:
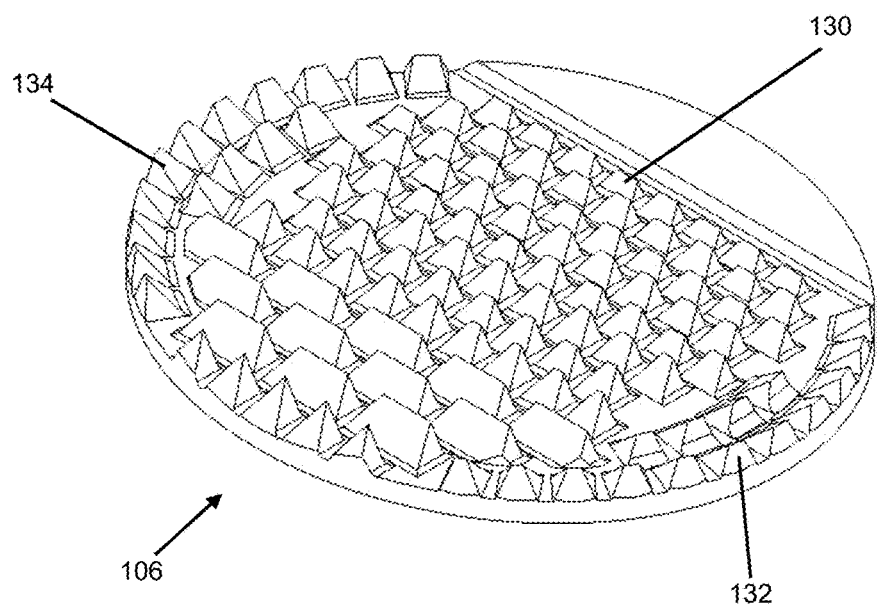
FIG. 12 is a first perspective view of the implant of FIG. 10.
Figure 13:
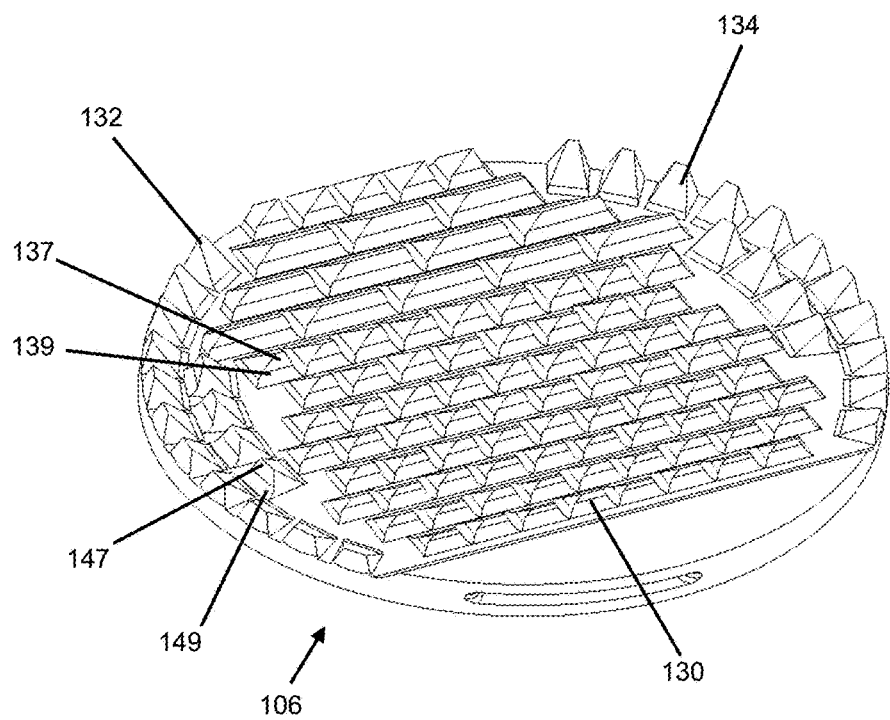
FIG. 13 is a second perspective view of the implant of FIG. 10.

While FIGS. 10, 12 and 13 illustrate that the superior resurfacing device 106 has a disc-like shape, it is possible for the superior resurfacing device 106 to have other shapes using the concepts of this invention.

The superior resurfacing device 106 may be defined as having a leading edge 110, a trailing edge 112, a first opposing side 114 and a second opposing side 116. The leading edge 110 is on the end of the superior resurfacing device 106 that is intended to be inserted first during the implantation process.

The trailing edge 112 may be oriented generally opposite from the leading edge 110. As such, the trailing edge 112 is the end of the superior resurfacing device 106 that enters a bodily space last during the implantation process.

The first opposing side 114 and the second opposing 116 are located on opposite edges of the superior resurfacing device 106. The first opposing side 114 and the second opposing side 116 extend between the leading edge 110 and the trailing edge 112.

The superior resurfacing device 106 may include a base web 120 and a plurality of teeth 122 that extend from the base web 120. The base web 120 defines opposing major surfaces that include a first major surface 124 and a second major surface 126.

In certain embodiments, the base web 120 may be formed with a relatively uniform thickness. In other embodiments, the base web 120 is tapered such that proximate the leading edge 110, the base web 120 is thicker than proximate the trailing edge 112. In certain embodiments, the angle of the taper is up to about 4 degrees. In other embodiments, the angle of the taper is about 2 degrees.

The first major surface 124 may be generally smooth to serve as an articulating surface, which articulates relative to a corresponding articulating surface of the inferior resurfacing device 108 when the first major surfaces 124 on the superior resurfacing device 106 and the inferior resurfacing device 108 are positioned adjacent to each other as illustrated in FIG. 11.

As such, the first major surface 124 can be referred to as the "articulating surface" of the superior resurfacing device 106. In certain embodiments, the articulating surface 124 may be coated with a separate layer that provides enhanced frictional (i.e., lower coefficient of friction) and/or wear characteristics.

The plurality of teeth 122 project from the second major surface 126 in a direction generally opposite the first major surface 124. In certain embodiments, the plurality of teeth 122 may include at least two groups of teeth. The teeth in each group of teeth may be shaped differently, oriented in a different direction and/or aligned differently than the teeth in the other groups of teeth.

While the description below is provided with respect to a particular configuration of teeth that is illustrated in the figures, a person of skill in the art will appreciate that various other configurations of teeth may be used that incorporate the concepts discussed below to reduce the potential of the superior and inferior resurfacing devices 106, 108 moving after implantation.

An important aspect of the teeth 122 is that they minimize the movement of the superior and inferior resurfacing devices 106, 108 with respect to the adjacent tissue. Such movement can include sliding out of the joint in which the superior and inferior resurfacing devices 106, 108 are implanted. Such movement can also include rotation of one of more of the superior and inferior resurfacing devices 106, 108 in the joint where the superior and inferior resurfacing devices 106, 108 implanted.

The first set of teeth 130 may resist movement of the superior resurfacing device 106 towards the trailing edge 112 such that the superior resurfacing device 106 moves out of the implant region in a direction that is opposite of the direction in which the superior resurfacing device 106 moved during the implantation process.

The first set of teeth 130 may be positioned at an intermediate location on the base web 120. As used herein, intermediate location means that the first set of teeth 130 is not located proximate the first opposing side 114 and the second opposing side 116. The first set of teeth 130 may also not be located proximate to the trailing edge 112. In certain embodiments, the first set of teeth 130 are positioned proximate the leading edge 110.

Alternatively, the first set of teeth 130 may be positioned to substantially cover the second major surface 126 such that the first set of teeth 130 are located proximate to the first opposing side 114 and the second opposing side 116.

The first set of teeth 130 may be positioned in a plurality of rows. These rows may be oriented generally transverse to a direction in which the superior resurfacing device 106 moves during the insertion process.

The teeth in adjacent rows of the first set of teeth 130 may be offset, as most clearly illustrated in FIG. 13. In certain embodiments, the teeth in a first row are placed so that the edges of the teeth in the first row are approximately aligned with a center of the teeth in a second row.

Using such a configuration of teeth enhances the ability of the superior resurfacing device 106 to resist movement after implantation because if the teeth in the first row cut a path through the tissue into which the teeth extend, the teeth in the second row will not also pass through the same path in the tissue. Rather, the teeth in the second row will have to cut a separate path through the tissue into which the teeth extend. Such a process requires more force than if the teeth in the second row move through the path formed in the tissue by the first row of teeth.

Alternatively or additionally, at least a portion of the teeth in the first set of teeth 130 may have a greater width. As used herein, width of the teeth is a direction that is generally perpendicular to the direction between the leading edge 110 and the trailing edge 112.

The teeth 130 having the greater width may also enhance the ability of the superior resurfacing device 106 to resist movement after implantation because the teeth 130 having the greater width engage the tissue over a larger area than the other teeth having a smaller width. In one such configuration, the teeth 130 with a greater width have a width that is about twice as large as the width of the teeth in the other portion of the first set of teeth 130.

The wider teeth 130 may also exhibit a greater resistance to deformation when subjected to a load placed thereon such as when it is attempted to slide the superior resurfacing device 106 with respect to the tissue into which the teeth 130 are implanted. Such greater resistance to deformation reduces the potential that the teeth 130 will deform to an extent where the teeth fail and/or that the superior resurfacing device 106 is permitted to move with respect to the tissue into which the teeth 130 are implanted.

In certain embodiments, the teeth 130 with the greater width may be positioned closer to the leading edge 110 than the other teeth in the first set of teeth 130 that have a smaller width. The teeth 130 with the greater width may be provided in more than one row. In certain embodiments, there are at least two rows of teeth 130 having a greater width.

The teeth in the different rows of the first set of teeth 130 may be formed so that the teeth in the rows proximate the leading edge 110 have a depth that is greater than a depth of the teeth in the rows proximate the trailing edge 112, as illustrated in FIG. 11. As used herein, depth of the teeth is a direction that is generally perpendicular second major surface 126.

In certain embodiments, the teeth in the rows proximate the leading edge 110 have a depth that is between about 80 percent and about 120 percent greater than a depth of the teeth in the rows proximate the trailing edge 112.

There may also be at least one intermediate row of teeth having a depth that is less than the depth of the teeth in the rows proximate the leading edge 110 and having a depth that is greater than the depth of the teeth in the rows proximate the trailing edge 112.

The teeth in the first set of teeth 130 may each have a leading face 133 and a trailing face 135. The leading face 133 is oriented towards the leading edge 110 while the trailing face 135 is oriented towards the trailing edge 112. An angle formed between the trailing face 135 and the base web 120 is less than an angle formed between the leading face 133 and the base web 120.

In certain embodiments, the angle formed between the leading face 133 and the base web 120 may be between about 20° and about 60°. In other embodiments, the angle formed between the leading face 133 and the base web 120 may be between about 30° and about 50°.

In certain embodiments, the angle formed between the trailing face 135 and the base web 120 may be between about 75° and about 105°. In other embodiments, the angle formed between the trailing face 135 and the base web 120 may be about 90°.

The teeth may also include a first side surface 136 and a second side surface 138. An angle formed between the first side surface 136 and the base web 120 may be between about 40° and about 80°. In other embodiments, the angle formed between the first side surface 136 and the base web 120 may be between about 60° and about 80°. The second side surface 138 may be oriented at an angle with respect to the base web 120 that is about the same as the angle between the first side surface 136 and the base web 120.

In other embodiments, the trailing face 135 may include an upper tooth section 137 and a lower tooth section 139 that are oriented in a non-collinear orientation with respect to each other, as illustrated in FIG. 13. In certain embodiments, an obtuse angle is formed between the upper tooth section 137 and the lower tooth section 139. In other embodiments, the angle between the upper tooth section 137 and the lower tooth section 139 is between about 135° and 170°.

As a result of this configuration, the upper tooth section 137 may be oriented at an angle with respect to the base web 120 that is greater than an angle between the lower tooth section 139 and the base web 120.

The first set of teeth 130 may include a plurality of leading edge teeth 141 that are positioned along the leading edge 110, as illustrated in FIGS. 10, 12 and 13. The teeth in the plurality of leading edge teeth 141 may have a width and a depth that is similar to the teeth positioned proximate to a center of the superior resurfacing device 106.

First and second side surfaces of the leading edge teeth 141 may be oriented at a smaller angle than the teeth positioned proximate to the center of the superior resurfacing device 106. This configuration provides the teeth in the leading edge teeth 141 with a pointer configuration than the other teeth in the first set of teeth 130.

Because the leading edge teeth 141 are positioned along the leading edge 110 and because of the curvature of the leading edge 110, the teeth in the leading edge teeth 141 may not all have the same depth, as most clearly illustrated in FIG. 10.

The second set of teeth 132 and the third set of teeth 134 enhance the ability of the superior resurfacing device 106 to resist being displaced side-to-side after implantation. Such movement may be in a direction that is angularly offset with respect to a direction in which the superior resurfacing device 106 moves during the implantation process.

While it is possible for the movement to be generally perpendicular to the direction in which the superior resurfacing device 106 moves during the implantation process, the second set of teeth 132 and the third set of teeth 134 may also prevent movement of the superior resurfacing device 106 in other directions that are not perpendicular to the direction in which the superior resurfacing device 106 moves during the implantation process.

The second set of teeth 132 are formed at or along the first opposing side 114. The individual teeth 140 in the second set of teeth 132 may be formed with a non-symmetrical relationship with respect to the teeth in the first set of teeth 130.

The second set of teeth 132 may be arranged in a plurality of rows. In certain embodiments, the second set of teeth 132 includes a first row of teeth 132a and a second row of teeth 132b. The first row of teeth 132a is positioned along the first opposing side 114. The second row of teeth 132b may be positioned between the first row of teeth 132a and the first set of teeth 130.

While it is illustrated that the teeth in the second set of teeth 132b are generally aligned with the teeth in the first set of teeth 132a, in certain embodiments, the teeth in the second set of teeth 132b may be offset from the teeth in the first set of teeth 132a similar to the manner in which adjacent rows of teeth in the first set of teeth 130 are offset from each other.

The second teeth 140 in the first row of teeth 132a may each have an exterior face 142a and an interior face 144a. The exterior face 142a faces the first opposing side 114 while the interior face 144a faces the second opposing side 116. An angle formed between the interior face 144a and the base web 120 is less than an angle formed between the exterior face 142a and the base web 120.

In certain embodiments, the angle formed between the exterior face 142a and the base web 120 may be between about 75° and about 105°. In other embodiments, the angle formed between the exterior face 142a and the base web 120 may be about 90°.

In certain embodiments, the angle formed between the interior face 144 and the base web 120 may be between about 20° and about 60°. In other embodiments, the angle formed between the interior face 144 and the base web 120 may be between about 30° and about 50°.

The second teeth 140 may also include a first side surface 146 and a second side surface 148. An angle formed between the first side surface 146 and the base web 120 may be between about 40° and about 80°. In other embodiments, the angle formed between the first side surface 146 and the base web 120 may be between about 60° and about 80°. The second side surface 148 may be oriented at an angle with respect to the base web 120 that is about the same as the angle between the first side surface 146 and the base web 120.

The teeth in the second row of teeth 132b may be shaped similarly to the teeth in the first row of teeth 132a in most respects. In one configuration, an angle between the exterior face 142b of the teeth in the second row of teeth 132b and the base web 120 may be less than an angle between the exterior face 142a of the teeth in the first row of teeth 132a and the base web 120.

In certain embodiments, the angle formed between the exterior face 142b of the teeth in the second row of teeth 132b and the base web 120 may be between about 60° and about 80°.

In other embodiments, the exterior face 142b of the teeth in the second row of teeth 132b includes an upper tooth section 147 and a lower tooth section 149 that are oriented in a non-collinear orientation with respect to each other. In certain embodiments, an obtuse angle is formed between the upper tooth section 147 and the lower tooth section 149.

As a result of this configuration, the upper tooth section 147 may be oriented at an angle with respect to the base web 120 that is greater than an angle between the lower tooth section 149 and the base web 120.

The third set of teeth 134 are formed at or along the second opposing side 116. The individual teeth 150 in the third set of teeth 134 may be formed with a non-symmetrical relationship with respect to the teeth in the first set of teeth 130.

The third set of teeth 134 may be arranged in a plurality of rows. In certain embodiments, the third set of teeth 134 includes a first row of teeth 134a and a second row of teeth 134b. The first row of teeth 134a is positioned along the second opposing side 116. The second row of teeth 134b may be positioned between the first row of teeth 134a and the first set of teeth 130.

While it is illustrated that the teeth in the second row of teeth 134b are generally aligned with the teeth in the first row of teeth 134a, in certain embodiments, the teeth in the second row of teeth 134b may be offset from the teeth in the first row of teeth 134a similar to the manner in which adjacent rows of teeth in the first set of teeth 130 are offset from each other.

The third teeth 150 in the first row of teeth 134a each have an exterior face 152 and an interior face 154. The exterior face 152 face the second opposing side 116 while the interior face 154 faces the first opposing side 114. An angle formed between the interior face 154 and the base web 120 is less than an angle formed between the exterior face 152 and the base web 120.

In certain embodiments, the angle formed between the exterior face 152 and the base web 120 may be between about 75° and about 105°. In other embodiments, the angle formed between the exterior face 152 and the base web 120 may be about 90°.

In certain embodiments, the angle formed between the interior face 154 and the base web 120 may be between about 20° and about 60°. In other embodiments, the angle formed between the interior face 154 and the base web 120 may be between about 30° and about 50°.

The third teeth 150 may also include a first side surface 156 and a second side surface 158. An angle formed between the first side surface 156 and the base web 120 may be between about 40° and about 80°. In other embodiments, the angle formed between the first side surface 156 and the base web 120 may be between about 60° and about 80°. The second side surface 158 may be oriented at an angle with respect to the base web 120 that is about the same as the angle between the first side surface 156 and the base web 120.

The teeth in the second row of teeth 134b may be shaped similarly to the teeth in the first row of teeth 134a in most respects. In one configuration, an angle between the exterior face 152b of the teeth in the second row of teeth 134b and the base web 120 may be less than an angle between the exterior face 152a of the teeth in the first group of teeth 134a and the base web 120.

In certain embodiments, the angle formed between the exterior face 152b of the teeth in the second row of teeth 142b and the base web 120 may be between about 60° and about 80°.

In other embodiments, the exterior face 152b of the teeth in the second row of teeth 134b includes an upper tooth section 157 and a lower tooth section 159 that are oriented in a non-collinear orientation with respect to each other. In certain embodiments, an obtuse angle is formed between the upper tooth section 157 and the lower tooth section 159.

As a result of this configuration, the upper tooth section 157 may be oriented at an angle with respect to the base web 120 that is greater than an angle between the lower tooth section 159 and the base web 120.

In some constructions, each tooth of the plurality of teeth can have an identical, or nearly identical, height. In other embodiments, the teeth can be formed with a tapered height such that the teeth proximate the leading edge 110 have a height that is greater than a height of the teeth proximate the trailing edge 112.

The height of the teeth may be tapered at an angle of up to about 4 degrees. In certain embodiments, the height of the teeth may be tapered at an angle of about 2 degrees. As a result of this configuration, the teeth proximate the leading edge 110 can establish a more rigid engagement with the corresponding tissue face to thereby resist displacement after insertion.

As described in greater detail below, a desired conformability characteristic of the superior resurfacing device 106 may be influenced by the overall thickness and the base web 120 to effectuate the desired degree of conformability. The overall thickness of the superior resurfacing device 106 may be selected by the treating clinician for insertion into a particular joint may vary as a function of other procedures associated with the insertion.

The conformability of the superior resurfacing device 106 may be enhanced by the layout of the teeth. In certain embodiments, the orientation of the first group of teeth 132 so that the teeth in adjacent rows are offset from each other may enhance the ability of the superior resurfacing device 106 to bend as compared to teeth configurations where teeth in adjacent rows are aligned with each other.

For example, the arrangement of the teeth in the offset configuration may provide the superior resurfacing device 106 with a greater number of folding axes than the configuration where teeth in adjacent rows are aligned with each other.

For example, where the superior resurfacing device 106 is inserted into a joint without any overt tissue removal prior to insertion, the overall thickness can be in the range of 0.5-2.5 mm. If, however, the insertion procedure entails first removing cartilage (or other tissue) from the joint, a thicker version of the superior resurfacing device 106 can be inserted, such that the overall thickness of the superior resurfacing device 106 is in the range of 0.5-3 mm.

The superior and inferior resurfacing devices 106, 108 may be integrally formed of a robust material that achieves desired conformability. The resurfacing body 46 in accordance with the present disclosure maintains its structural integrity (i.e., little or no wear) without adhesive or cohesive damage when subjected to typical articulation of the joint with movement of the patient.

In some constructions, the superior and inferior resurfacing devices 106, 108 are formed of an implantable-grade plastic, although other materials such as metal are also available. For example, the superior and inferior resurfacing devices 106, 108 can be made from the polyetherketone (PEK) family of plastics, which have strength, wear, flexibility, and biocompatibility properties appropriate for insertion into, and long-term functioning within, the joint.

Polyetheretherketone (PEEK) has surprisingly been found to provide not only the conformability attributes described below, but also long-term mechanical strength and resistance to wear. Additional material(s) can be incorporated, such as those exhibiting radio-opacity properties. For example, the superior and inferior resurfacing devices 106, 108 can be formed from a radio-opaque mineral (e.g., barium)-loaded PEK composition.

Visualization can also be provided via one or more radio-opaque marker bands (e.g., platinum marker band). The visualization marker 170 can be embedded within at least one of the superior and inferior resurfacing device 106, 108 (e.g., a radio-opaque rod inserted into a hole formed in the superior and inferior resurfacing device 106, 108). In another configuration, the radio-opaque material may be inserted along a portion of a perimeter of the superior and inferior resurfacing device 106, 108.

In another configuration of the visualization marker 170 indicates not only the location of the superior and inferior resurfacing device 106, 108 but also the orientation of the superior and inferior resurfacing device 106, 108 with respect to each other.

One such configuration of the visualization marker 170 includes two marker portions 172, 174 that are oriented at an angle with respect to each other. A first marker portion 172 may be oriented at an angle with respect to the second marker portion 174 that is between about 60 degrees and about 100 degrees. In certain embodiments, the angle between the first marker portion 172 and the second marker portion 174 is between about 70 degrees and about 80 degrees.

The first marker portion 172 may be positioned proximate to a central axis of the superior resurfacing device 106 that is intermediate the first opposing side 114 and the second opposing side 116.

An aperture 180 may be formed from the trailing edge 112 of the superior resurfacing device 106 that has a depth that is greater than a length of the first marker portion 172. The aperture 180 has a diameter that is slightly larger than the diameter of the first marker portion 172.

Adjacent to and intersecting with the aperture 180 is a channel 182 that has a length that is slightly larger than a length of the second marker portion 174. The channel 182 has a width that is slightly larger than the width of the second marker portion 174.

Forming the aperture 180 and the channel 182 with the preceding dimensions enables the visualization marker 170 to be recessed beneath the side of the superior resurfacing device 106 after insertion of the first marker portion 172 into the aperture 180 and the second marker portion 174 into the channel 182.

A sealant (not shown) may be placed over the visualization marker 170 to retain the visualization marker 170 in a stationary position with respect to the superior resurfacing device 106. The sealant should resist degradation after the superior and inferior resurfacing devices 106, 108 are implanted. The sealant should also be selected to minimize the potential of adverse interactions after the superior and inferior resurfacing devices 106, 108 are implanted.

Since the superior and inferior resurfacing devices 106, 108 are formed substantially similar to each other and the superior and inferior resurfacing devices 106, 108 are implanted with the articulating surfaces facing each other, the first marker portion in the superior and inferior resurfacing devices 106, 108 are aligned with each other during the insertion process.

In view of the preceding comments, if during evaluation of the position of the superior and inferior resurfacing devices 106, 108 using the visualization marker 170 indicates that the first marker portions 172 in the superior and inferior resurfacing device 106, 108 are not aligned with each other, it will be possible to determine that at least one of the superior and inferior resurfacing devices 106, 108 are not correctly oriented.

When the superior and inferior resurfacing devices 106, 108 are inserted correctly, the second marker portions 174 will be directed opposite from each other. The two visualization markers 170 thereby provide a generally T-shape. If the second marker portions 174 do not form the top of the T-shape using a radio-opaque detection technique, it can be determined that the superior and inferior resurfacing devices 106, 108 are not correctly inserted. For example, if the visualization markers 170 in the superior and inferior resurfacing devices 106, 108 form an L-shape, it can be determines that the articulating surface on the superior resurfacing device 106 is not facing the articulating surface on the inferior resurfacing device 108.

Depending on a thickness of the superior resurfacing device 106 proximate the trailing edge 112, there may not be teeth positioned on the superior resurfacing device 106 proximate the trailing edge 112, such as illustrated in FIGS. 13-16. For example, to accommodate the visualization marker 170, the base web 120 may need to be formed with a thickness proximate the trailing edge 112 than in the other portions of the superior resurfacing device 106 where the visualization marker 170 is not implanted therein.

The selected materials, shapes, and dimensions associated with the superior and inferior resurfacing devices 106, 108 impart or create a conformability property that allows the superior and inferior resurfacing devices 106, 108 to "match" the multi-planar concavity associated with a native joint articular face anatomy.

In general terms, "conformability" is inversely proportional to bending stiffness of the superior and inferior resurfacing device 106, 108 during insertion, and may be increased as the superior resurfacing device 106, 108 heats to body temperature and is allowed to creep.

With the above understandings in mind, the conformability characteristic of the superior and inferior resurfacing devices 106, 108 is sufficient such that the superior and inferior resurfacing devices 106, 108 readily transition from the relatively flat state illustrated in FIGS. 13-16 to an inserted state (not shown) in which the superior and inferior resurfacing devices 106, 108 substantially matches or mimics the naturally-occurring shape (e.g., radius of curvature of curved portions) of the joint face to which the superior and inferior resurfacing devices 106, 108 are secured. In this regard, the joint is subject to, or experiences, various loads that effectuate compressive forces at the region of interface between the superior and inferior articular faces.

Compressive loads normal to and across the articular faces will be generated upon separation/posterior translation of the superior articulating joint due to joint capsule tensioning. The conformable nature of the superior and inferior resurfacing devices 106, 108 is such that in the presence of these typical compressive forces, the superior and information resurfacing devices 106, 108 will transition from the relatively flat state to the inserted state in which the superior and inferior resurfacing devices 106, 108 substantially matches the geometry of the joint surface to which the superior and inferior resurfacing devices 106, 108 are secured (i.e., the superior and inferior resurfacing devices 106, 108 will flex to conform with a macroscopic shape/contour of the native articular face to which the superior and inferior resurfacing device 106, 108 are applied, but may not conform to the microscopic variations in the native articular face, for example small deviations due to cartilage defects, bony fissures, or small voids during preparation of the joint (typically 0.05-0.5 mm in width)).

This process will occur as the compressive forces applied by the ends of the hypothetical concave region of one articular surface (e.g., the superior articular surface) and the center of the corresponding convex surface on the opposing articular (e.g., the inferior articular surface) generate a bending moment on the superior and inferior resurfacing device 106, 108 that produces strain to conform the superior and inferior resurfacing devices 106, 108 to the native anatomy.

Figure 14:
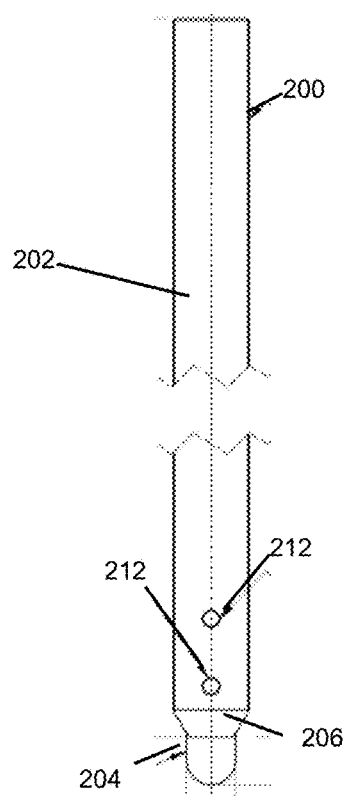
FIG. 14 is a top view of a guide probe assembly according to an embodiment of the invention.
Figure 15:
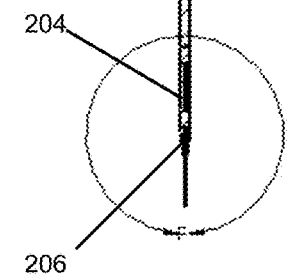
FIG. 15 is a sectional view of the guide probe assembly taken along a line A-A in FIG. 14.

In certain embodiments, a guide probe assembly 200, as illustrated in FIGS. 14 and 15, may be initially used to locate the region in the facet joint where the resurfacing device 46 is to be inserted. The guide probe assembly 200 may include a guide probe shaft 202 and a guide probe tip 204 that extends from a distal end of the guide probe shaft 202.

The guide probe shaft 202 may have a substantially rectangular profile, as illustrated in FIGS. 14 and 15. Forming the guide probe shaft 202 with the substantially rectangular profile enables the guide cannula 260 to slide over the guide probe assembly 200 after the guide probe assembly 200 is positioned with the guide probe tip 204 at least partially in the facet joint, as is discussed in more detail herein. This process reduces the time associated with implanting the resurfacing body 46 when compared to an implantation system that does not utilize this insertion process.

To minimize the size of the incision that is formed in the patient, the guide probe shaft 202 may be formed with a width and a height that is approximately equal to a width and a height of the resurfacing body 46.

In certain embodiments, the guide probe shaft 202 has a width of between about 5 millimeters and about 20 millimeters. In other embodiments, the guide probe shaft 202 has a width of about 12 millimeters.

In certain embodiments, the guide probe shaft 202 has a thickness of between about 0.20 millimeters and about 10 millimeters. In other embodiments, the guide probe shaft 202 has a thickness of about 2 millimeters.

The guide probe shaft 202 is formed with a length that enables a proximal end of the guide probe shaft 202 to be positioned outside of the patient's body when the distal end of the guide probe shaft 202 is adjacent the facet joint. Such a configuration facilitates the surgeon or other person who is using the guide probe assembly 200 to accurately position the guide probe assembly 200 with respect to the facet joint.

In certain embodiments, the guide probe shaft 202 has a length of between about 10 centimeters and about 30 centimeters. In other embodiments, the guide probe shaft 202 has a length of about 23 centimeters.

The distal end of the guide probe shaft 202 may include a tapered region 206, as illustrated in FIGS. 14 and 15, to provide a transition between the guide probe shaft 202 and the guide probe tip 204. The length of the tapered region 206 may depend on a variety of factors such as a difference in the width and the height of the guide probe shaft 202 and the guide probe tip 204.

The guide probe shaft 202 may be fabricated from a relatively rigid material to facilitate the use of the guide probe shaft 202 to locate the facet joint using the guide probe tip 204. In certain embodiments, the guide probe shaft 202 may be fabricated from stainless steel. In other embodiments, it is possible to fabricate the guide probe shaft 202 from a non-metallic material such as plastic.

An important criterion is that the guide probe shaft 202 be fabricated from a material that is biocompatible. If it is desired to reuse the guide probe shaft 202 for multiple surgical procedures, the guide probe shaft 202 should be capable of withstanding repeated sterilization processes such as by using an autoclave.

The guide probe tip 204 is operably connected to the proximal end of the guide probe shaft 202. In certain embodiments, the guide probe shaft 202 has an aperture 210 formed in the distal end thereof. This aperture 210 is adapted to receive a portion of the guide probe tip 204.

The portion of the guide probe tip 204 that extends into the aperture 210 may have a length that is greater than a length of the guide probe tip 204 that extends beyond the proximal end of the guide probe shaft 202 to enhance the ability of the guide probe tip 204 when attempting to locate a desire location in the facet joint.

Forming the guide probe tip 204 separate from the other portions of the guide probe assembly 200 enables guide probe tips 202 having different widths and/or lengths to be used depending on the size, shape and location of the facet joint in which the resurfacing device is being inserted.

The guide probe tip 204 may have a thickness and a width that are both smaller than a thickness and a width of the guide probe shaft 202. In certain embodiments, the guide probe tip 104 has a width of between about 5 millimeters and about 20 millimeters. In other embodiments, the guide probe tip 104 may have a width that is about 9 millimeters.

In certain embodiments, the guide probe tip 204 may have a thickness of between about 0.10 millimeters and about 0.50 millimeters. In other embodiments, the guide probe tip 204 may have a thickness of about 0.20 millimeters.

The guide probe tip 204 may be formed with a proximal end that is not pointed. Forming the guide probe tip 204 with this configuration at the proximal end minimizes the potential that the guide probe tip 204 will damage or other negatively impact the tissue in the facet joint or surrounding the facet joint.

In certain embodiments, it is possible for the proximal end of the guide probe tip 204 to be sharpened such that the guide probe tip 204 may be used to cut tissue when attempting to access the facet joint.

The guide probe tip 204 may be fabricated from a material that is rigid but which is flexible. Forming the guide probe tip 204 from a flexible material enhances the ability of the guide probe tip 204 to be positioned at least partially in the facet joint as an initial step in implanting the resurfacing body 46.

In certain embodiments, the guide probe tip 204 is fabricated from a metallic material such as stainless steel. It is also possible to fabricate the guide probe tip 204 from a non-metallic material using the concepts of the invention.

An important criterion is selecting the material that is used to fabricate the guide probe tip 204 is that the material be biocompatible. If it is desired to reuse the guide probe tip 204 for multiple surgical procedures, the guide probe tip 204 should be capable of withstanding repeated sterilization processes such as by using an autoclave.

The guide probe tip 204 may be attached to the guide probe shaft 202 using at least one fastening device 212. In certain embodiment at least two of the fastening devices 212 are used to attached the guide probe tip 204 to the guide probe shaft 202.

The fastening device 212 may have a variety of different configurations. In one configuration, the fastening device 212 frictionally engages the guide probe shaft 202 through the aperture formed therein. Alternatively, the fastening device 212 may have a threaded side surface that enables the fastening device 212 to be screwed into the guide probe shaft 202 having an aperture with a complementary shape.

Figure 16:
FIG. 16 is an enlarged sectional view of a tip portion of the guide probe assembly.

As an alternative to the configuration of the guide probe assembly 200 configuration illustrated in FIGS. 14-16, alternative configurations of the guide probe assembly 200 may be utilized in conjunction with the concepts of the invention. One such alternative configuration of the guide probe assembly is illustrated at 240 in FIG. 17. The guide probe assembly 240 includes an elongated main portion 242 and a handle portion 244 that is attached to a proximal end of the main portion 242.

Figure 17:
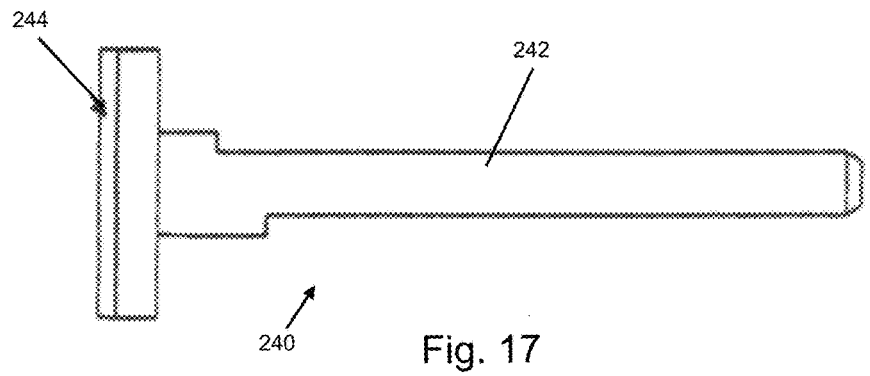
FIG. 17 is a side view of a guide probe assembly according to an alternative embodiment of the invention.

The main portion 242 may have a configuration that is similar to the guide probe shaft 202 illustrated in FIGS. 14 and 15. While FIG. 17 illustrates that the main portion 242 does not have a separate tip portion, it is possible to adapt the concepts of this embodiments to encompass a separate tip portion so that the tip portion may possess different physical characteristics that the main portion 242 from which the tip portion extends. Even when a separate tip portion is not provided, a proximal end of the main portion 242 may be tapered to facilitate guiding the guide probe assembly 240 to a desired location in the facet joint.

The handle portion 244 enhances the ability to grasp the guide probe assembly 240 during the insertion process. In certain embodiments, the handle portion 244 may have a width that is greater than a width of the main portion 242. The handle portion 244 may also have a thickness that is greater than a thickness of the main portion 242.

The guide probe assembly 240 may be used in conjunction with the guide probe assembly 200. In such a configuration, the main portion 242 may be placed adjacent to the guide probe assembly 200. When used in this configuration, the main portion 242 and the guide probe assembly 200 may be thinner than with the separately used configuration so that the main portion 242 and the guide probe assembly 200 may both fit inside of the guide cannula 260.

This configuration may utilize the handle portion 244 for guiding the distal end of the guide probe assembly 200 into a position within the facet joint. Thereafter, the guide probe assembly 240 may be withdrawn. Next, the guide cannula 260 may be placed over the guide probe assembly 200.

Figure 18:
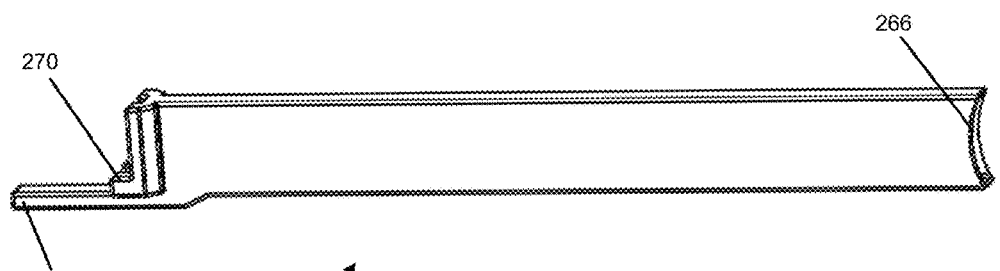
FIG. 18 is a perspective view of a guide cannula for use in conjunction with an embodiment of the invention.

The delivery system may include a guide cannula 260, as illustrated in FIGS. 18 and 15. The guide cannula 260 has an internal passage 262 that extends from a proximal end to a distal end thereof. In certain embodiments, the passage 262 may have a generally rectangular configuration.

A width of the passage 262 is smaller than a width of the delivery cannula 280. In certain embodiments, the width of the passage 262 may be between about 3 millimeters and about 15 millimeters. In other embodiments, the width of the passage 262 is between about 5 millimeters and about 10 millimeters.

A height of the passage 262 is smaller than a height of the delivery cannula 280. In certain embodiments, the height of the passage 262 may be between about 0.50 millimeters and about 5 millimeters. In other embodiments, the height of the passage 262 is about 2 millimeters.

To facilitate accurately positioning the guide cannula 260 with respect to the facet joint, the proximal end of the guide cannula 260 may have a concave surface 266. The concave surface 266 may at least partially receive a convex surface of the facet joint to thereby prevent the guide cannula 260 from moving laterally with respect to the facet joint and thereby enhance the ability to accurately insert the resurfacing device into the facet joint.

The guide cannula 260 may include a first stop mechanism 270 proximate a distal end thereof. The first stop mechanism 270 limits a distance the delivery cannula 280 may be inserted into the guide cannula 260. In certain embodiments, the first stop mechanism 270 engages a stop surface 286 that extends from an outer surface of the delivery cannula 280 proximate a distal end thereof.

The guide cannula 260 may also include a second stop mechanism 272 extending from the proximal end thereof. The second stop mechanism 272 limits a distance the implant insertion tool 300 may be inserted into the guide cannula 260 to thereby prevent over-insertion of the resurfacing device 46 into the facet joint. The second stop mechanism 272 may engage a shoulder 320 on the implant insertion tool 310 when the implant insertion tool 310 has been extended a desired distance into the guide cannula 260.

To enhance the ability to use the different components of the system, the second stop mechanism 272 may be positioned in a spaced-apart relationship with respect to the first stop mechanism 270. In certain embodiments, a spacing between the first stop mechanism 270 and the second stop mechanism 272 is between about 1 centimeter and about 5 centimeters.

The guide cannula 260 thereby facilitates extending the guide probe shaft 202 into the proximal end of the rectangular passage 262 until the proximal end of the guide cannula 260 is adjacent to the facet joint. Thereafter, the guide probe assembly 200 may be withdrawn from the guide cannula 260 by pulling the distal end of the guide probe assembly 200.

The guide cannula 260 may be fabricated with a length that enables the distal end to be positioned proximate to the facet joint where the implant is to be inserted while the proximal end is positioned outside of the person's body. In certain embodiments, the guide cannula 260 may have a length of between about 10 centimeters and about 30 centimeters.

The delivery cannula 280 may have a generally rectangular profile with a width and a height that are both slightly smaller than the width and the height of the guide cannula 260. This configuration enables the delivery cannula 280 to be inserted into the guide cannula 260 after the guide stop assembly 200 has been removed from the guide cannula 260.

The delivery cannula 280 has an internal passage 282 that extends from a proximal end to a distal end thereof. In certain embodiments, the passage 282 may have a generally rectangular configuration.

A width of the passage 282 is smaller than a width of the main portion 312 of the implant insertion tool 310. In certain embodiments, the width of the passage 282 may be between about 3 millimeters and about 15 millimeters. In other embodiments, the width of the passage 282 is between about 5 millimeters and about 10 millimeters.

A height of the passage 282 is smaller than a height of the main portion 312 of the implant insertion tool 310. In certain embodiments, the height of the passage 282 may be between about 0.5 millimeters and about 5 millimeters. In other embodiments, the height of the passage 282 is about 2 millimeters.

Figure 19:
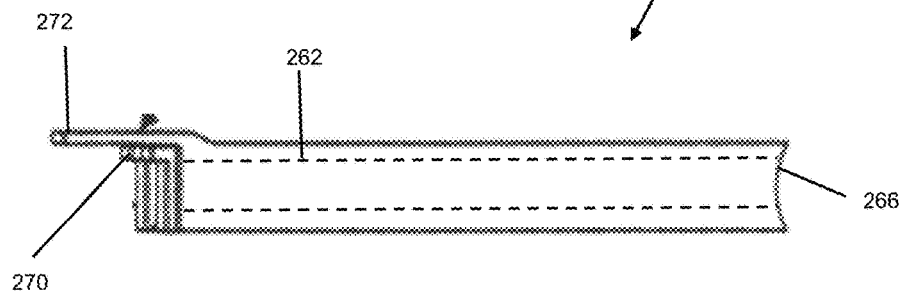
FIG. 19 is a side view of the guide cannula of FIG. 18.

Proximate the proximal end of the delivery cannula 280, the sides of the passage 282 may be removed so that an upper face and a lower face of the delivery cannula 280 define a pair of arms. When the implant insertion tool 310 is inserted into the delivery cannula 280, at least a part of the shoulder portion 320 may have a width that is greater than the width of the delivery cannula 280, as illustrated in FIG. 19. This configuration thereby limits the distance that the implant insertion tool 310 may be inserted into the delivery cannula 280.

The delivery cannula 280 may include a pair of leaflets 284 that extend from a distal end thereof. The leaflets 284 may be fabricated from a resilient material. The leaflets 284 may be initially positioned adjacent each other.

The leaflets 284 may have a width that is approximately the same as a width of the resurfacing body 46. A distal end of the leaflets 284 may be curved. The curved distal end of the leaflets 284 thereby minimizes damage to the superior articular face and the inferior articular face of the facet joint as the leaflets are moved into a position at least partially within the facet joint to provide an opening in the facet joint that is adapted to receive the resurfacing body 46.

The leaflets 284 may deflect away from each other as the resurfacing body 46 and the distal end of the implant insertion tool 310 extend therebetween. The leaflets 284 thereby enable maintaining the resurfacing body 46 in engagement with the implant insertion tool 310.

The force required to separate the leaflets 284 should be sufficiently large so that the leaflets 284 are retained in the closed configuration. However, the force should not be too great such that it is difficult for the resurfacing body 46 to be urged between the leaflets 284 during the implantation process or that the leaflets 46 damage the resurfacing body 46 when passing between the leaflets 284.

Proximate the proximal end of the delivery cannula 280, a stop mechanism 286 may extend from at least one outer surface of the delivery cannula 280. The stop mechanism 286 may be an elevated region that is oriented generally transverse to an axis of the delivery cannula 280.

In certain embodiments, the stop mechanism 286 may comprise two elevated regions that are mounted in a spaced-apart configuration, as illustrated in FIG. 20. The two elevated regions thereby define a channel 288 that extends therebetween. The channel 288 is adapted to receive a portion of a leaflet retractor tool 360, which may be used to withdraw the delivery cannula 280 from the guide cannula 260.

The stop mechanism 286 engages the first stop mechanism 270 on the guide cannula 260. The stop mechanism 286 thereby limits a distance to which the delivery cannula 280 may be inserted into the guide cannula 260.

An embodiment of the invention may also include an implant insertion tool 310, as illustrated in FIG. 21. The implant insertion tool 310 may include a main portion 312 and a handle portion 314 that is attached to a proximal end of the main portion 312.

The main portion 312 may have a width and a height that are slightly smaller than the width and the height of the delivery cannula 280. This configuration enables the main portion 312 to be placed inside of and slide with respect to the delivery cannula 280 during the process of inserting the resurfacing body 46.

In certain embodiments, the width of the main portion 312 may be between about 3 millimeters and about 15 millimeters. In other embodiments, the width of the main portion 312 is between about 1 millimeter and about 5 millimeters.

In certain embodiments, the height of the main portion 312 may be between about 0.5 millimeters and about 5 millimeters. In other embodiments, the width of the main portion 312 is about 2 millimeters.

Proximate the intersection with the handle portion 314, the main portion 312 may include a shoulder 320 extending from at least one side thereof. The shoulder 320 may be used to limit a distance to which the implant insertion tool 310 may be inserted into the delivery cannula by engaging the second stop mechanism 272 on the guide cannula 260.

The handle portion 314 may be oriented generally perpendicular to the main portion 312. The handle portion 314 thereby provides an enlarged surface that may be used to grasp the implant insertion tool 310 and thereby facilitates manipulating the implant insertion tool 310. In certain embodiments, the length of the handle portion 314 may be between about 5 centimeters and about 15 centimeters.

A distal end 322 of the main portion 312 may include a concave surface 323 that is curved to at least partially conform to a surface of the resurfacing body 46. The concave surface thereby enhances the ability to retain the resurfacing body 46 in a desired position with respect to the implant insertion tool 310

To further enhance the ability to maintain the resurfacing body 46 in a desired location with respect to the implant insertion tool 310, an extension 324 may extend from the distal end 322. The extension 324 is adapted to engage the engagement feature 80 that is provided in the resurfacing body 46.

The extension 324 may have a shape that is similar to but slightly smaller than the engagement feature 80. In particular, the extension 324 may include a first extension region 326a and a second extension region 326b.

The first extension region 326a has a width that is smaller than the width of the first aperture region 81a. The second extension region 326b has a width that is larger than the width of the first aperture region 81a and smaller than the width of the second aperture region 81b. This configuration enables the extension 324 to be retained in the engagement feature 80 to prevent the resurfacing body 46 from being separated from the implant insertion tool 310. More details on the relative size of the engagement feature 80 and the extension 324 are discussed above.

Figure 25:
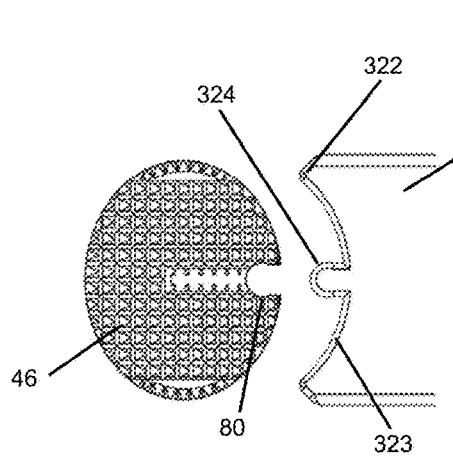
FIG. 25 is a top view of the resurfacing device positioned adjacent to a distal end of the implant insertion tool.
Figure 26:
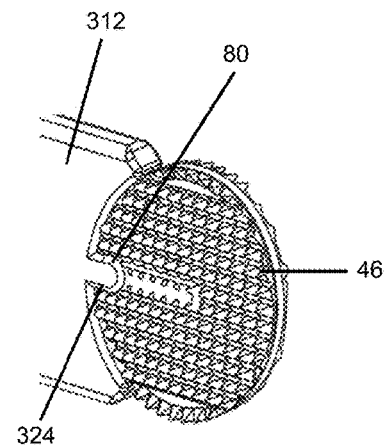
FIG. 26 is a perspective view of the resurfacing device in engagement with an extension on the distal end of the implant insertion tool.

FIGS. 25 and 26 illustrate the relationship between the resurfacing body 46 and the implant insertion tool 310. In FIG. 25, the resurfacing body 46 is placed adjacent to but spaced-apart from the implant insertion tool 310. In FIG. 26, the resurfacing body 46 is in engagement with the implant insertion tool 310 such that the extension 324 extends into and engages the engagement feature 80. The shape of the engagement feature 80 may be approximately the same as the shape of the extension 324.

Since the accurate placement of the resurfacing body 46 within the facet joint plays an important role in successfully treating the patient, the implant insertion tool 310 is configured to be inserted into the delivery cannula 280 and the guide cannula 260 until the handle portion 314 engages the second stop mechanism 272 on the guide cannula 260. This configuration protects against inadvertent over insertion of the resurfacing body 46.

Figure 23:
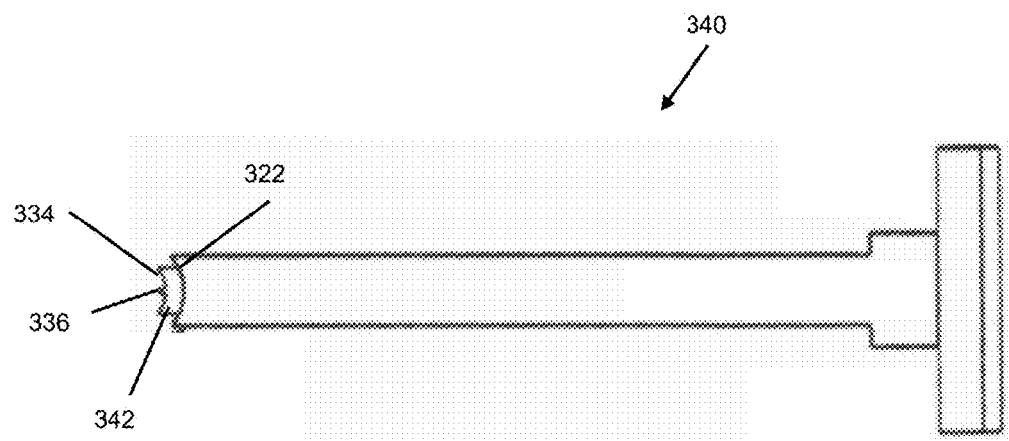
FIG. 23 is a side view of an implant insertion tool according to another alternative embodiment of the invention.

In certain situations depending on the shape of the facet joint where the resurfacing body 46 is being implanted, it may be desired to insert the resurfacing body 46 to different distances in the facet joint. To facilitate accurately inserting the resurfacing body 46 to a desired depth, embodiments of the invention utilize implant insertion tools 330 and 340, as illustrated in FIGS. 22 and 23. These implant insertion tools 330, 340 provide for selected countersinking of the resurfacing body 46 in the facet joint.

Other than the features set forth below, the implant insertion tools 330, 340 have a similar configuration to the implant insertion tool 310 illustrated in FIG. 17. The implant insertion tool 330 in FIG. 18 includes a countersink extension 332 that extends from the distal end thereof. The countersink extension 332 may have a concave end surface 334 that with a curvature that is similar to a curvature of the resurfacing body 46.

Similar to the embodiment in FIG. 21, an extension 336 is provided on the countersink extension 332 that facilitates attachment of the resurfacing implant 46 to the implant insertion tool 330.

The end surface 334 is spaced apart from the concave surface 322. In certain embodiments, the distance between the end surfaces may be between about 1 millimeter and about 10 millimeters. In other embodiments, the distance between the end surfaces may be about 3 millimeters.

The countersink extension 332 may have a width and a height that are smaller than the width and the height of the main portion 312. Such a configuration minimizes the potential of contact between the countersink extension 332 and the tissue within the facet joint, as such contact could cause undesirable side effects.

The implant insertion tool 340 in FIG. 23 is similar to the implant insertion tool 330 in FIG. 22 except that the countersink extension 342 is slightly longer. In certain embodiments, the countersink extension 342 may have a length of about 5 millimeters.

Figure 24:
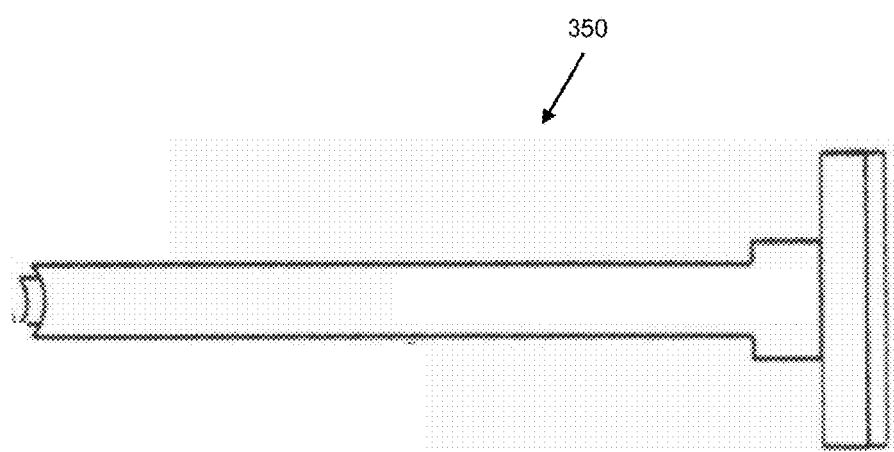
FIG. 24 is a side view of an implant countersink positioner according to an embodiment of the invention.

It is also possible to utilize a countersink positioner 350, as illustrated in FIG. 24 in conjunction with positioning the resurfacing body 46 at a desired location within the facet joint. The countersink positioner 350 is similar to the implant insertion tool 330 illustrated in FIG. 22 except that the countersink positioned 350 does not include an extension extending from a distal end thereof.

The countersink positioner 350 may thereby be utilized after the resurfacing body 46 has been inserted into the facet joint when it is recognized that the resurfacing body 46 is not inserted far enough into the facet joint. After removing the implant insertion tool 310 from the delivery cannula 280, the countersink positioner 350 is inserted into the delivery cannula 280.

Similar to the handle portion 314 on the implant insertion tool 310 limiting a distance that the implant insertion tool 310 may be inserted into the delivery cannula 280, the handle portion 352 on the countersink positioner 350 limits the distance that the countersink positioner 350 may be inserted into the delivery cannula 280 so that the resurfacing body 46 may be accurately positioned within the facet joint.

In operation, an incision is made in the patient proximate to the facet joint where it is desired to implant the resurfacing body 46. The guide probe assembly 200 is inserted into the patient so that the guide probe tip 204 can be used to identify the joint line in the facet joint.

Figure 27:
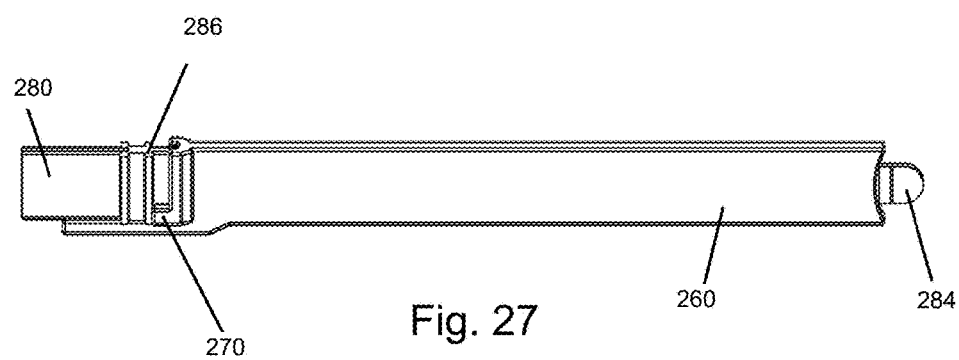
FIG. 27 is a perspective view of the delivery cannula inserted into the guide cannula.

Next, the guide cannula 260 is slid over the guide probe assembly 200, as illustrated in FIG. 27, until the distal end of the guide cannula 260 is adjacent to the facet joint. The guide probe assembly 200 thereby enables the guide cannula 260 to be accurately and quickly placed in the location for the implanting process.

Figure 28:
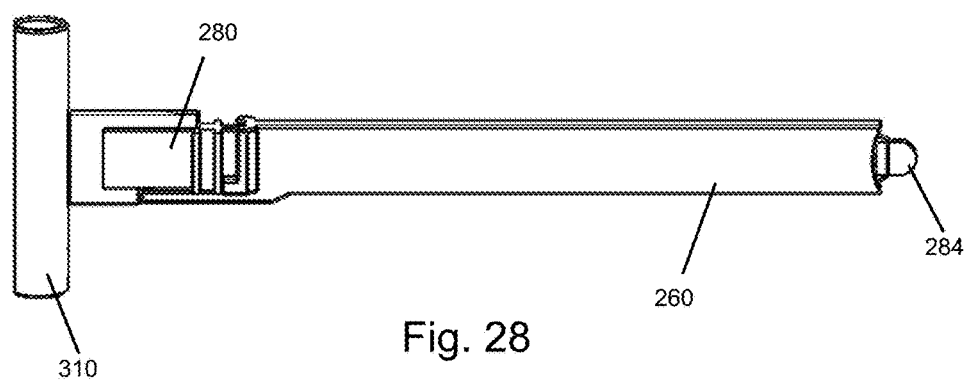
FIG. 28 is a perspective view of the implant insertion tool in an initial position where the resurfacing device is inside of the delivery cannula and where the delivery cannula is inside of the guide cannula.

The guide probe assembly 200 is then withdrawn from the guide cannula 260 with care being exercised to maintain the guide cannula 260 in a stationary position with respect to the facet joint. Thereafter, the delivery cannula 280 is inserted into the guide cannula 260 until a rib 281 on the delivery cannula 280 engages the first stop mechanism 270, as illustrated in FIG. 28. The first stop mechanism 270 thereby limits the distance to which the delivery cannula 280 may be inserted into the guide cannula 260.

In this configuration, the leaflets 284 extend from the distal end of the guide cannula 260. As the distal end of the guide cannula 260 is adjacent to the facet joint, the leaflets 284 extend into the facet joint to cause a region to be formed where the resurfacing body 46 may be inserted in subsequent operations.

Next, the resurfacing body 46 is positioned adjacent to the distal end of the implant insertion tool 310 so that the extension 324 extends into the engagement feature 80, as illustrated in FIG. 26. The implant insertion tool 310 is then inserted into the proximal end of the delivery cannula 280.

Figure 29:
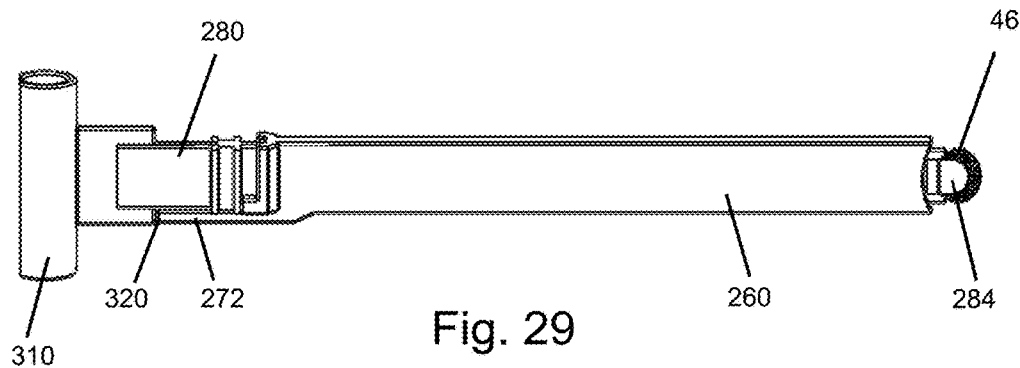
FIG. 29 is a perspective view of the implant insertion tool in an inserted position where the resurfacing device is partially extending beyond the distal end of the delivery cannula.

When the implant insertion tool 310 is almost completely inserted into the delivery cannula 280, the resurfacing body 46 is recessed in the delivery cannula 280, as illustrated in FIG. 29.

In some embodiments, it may be desirable to use a leaflet spreader (not shown) that maintains the leaflets 284 in a spaced apart configuration such that the resurfacing body 46 may be positioned between the leaflets 284. If it is desired to use the leaflet spreader, the loading process may be changed slightly so that the resurfacing body 46 is attached to the implant insertion tool 310 and then the implant insertion tool 310 is inserted into the delivery cannula 280.

Figure 30:
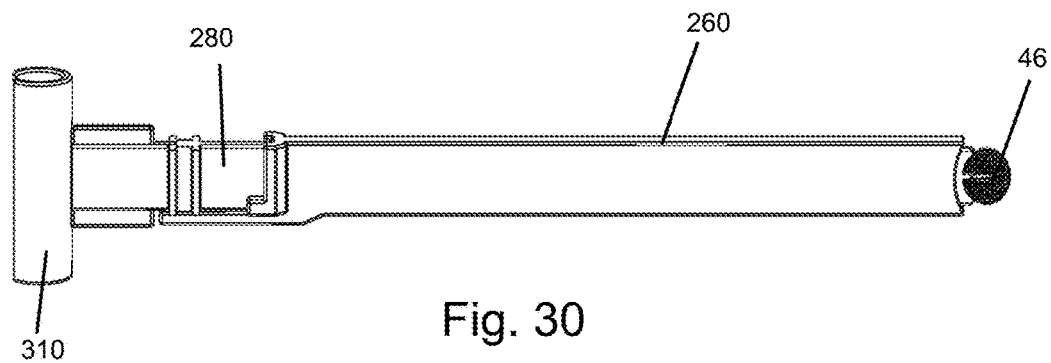
FIG. 30 is a perspective view of the implant insertion tool in a partially retracted position where the resurfacing device is moved beyond the delivery cannula for implanting the resurfacing device in the facet joint.

The insertion of the implant insertion tool 310 is continued until the resurfacing body 46 begins to extend from the distal end of the delivery cannula 280, as illustrated in FIG. 30. At this time, the shoulder 320 engages the second stop mechanism 272 to limit the distance to which the implant insertion tool 310 may be inserted into the delivery cannula 280. As noted above, the leaflets 284 are deflectable to provide a space for the resurfacing body 46 to be inserted into the facet joint.

Next, the delivery cannula 280 is urged away from the facet joint, as illustrated in FIG. 30. This motion causes the leaflets 284 to be refracted to within the delivery cannula 280. The facet joint returns to its initial position, which causes the resurfacing body 46 to fill the space between the bones.

Figure 31:
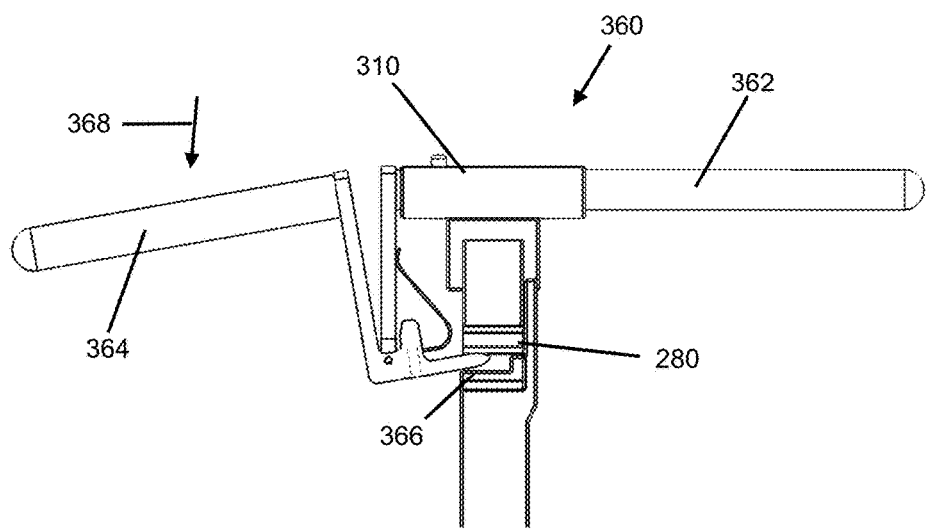
FIG. 31 is a side view of a leaflet retractor tool for use in withdrawing the implant insertion tool from the delivery cannula.
Figure 32:
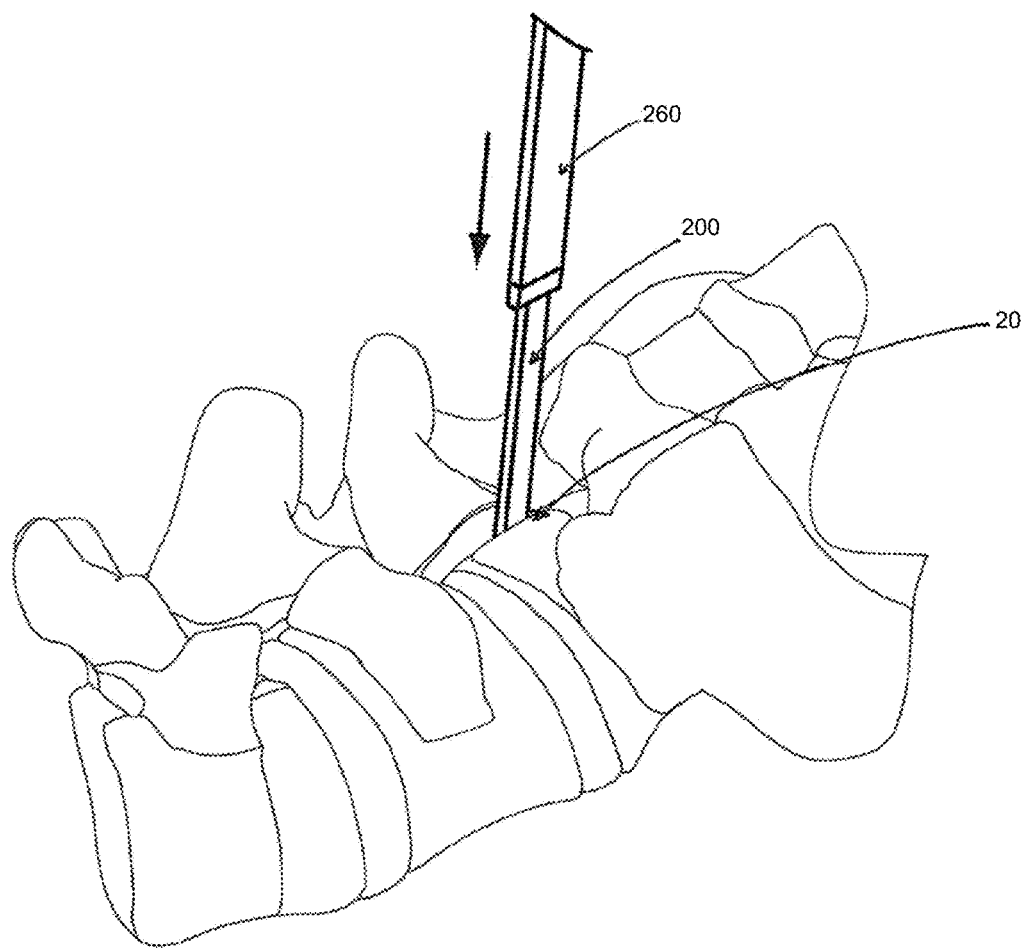
FIG. 32 is a perspective view of the guide probe assembly inserted into the facet joint and the guide cannula being inserted over the guide probe assembly.

In certain circumstances, it may be desirable to use a leaflet retractor tool 360 such as is illustrated in FIG. 31 to cause the delivery cannula 280 to be urged away from the facet joint. The leaflet refractor tool 360 includes a first handle section 362 and a second handle section 364 that are pivotally mounted with respect to each other.

The first handle section 362 engages the handle portion 314 on the implant insertion tool 310. In certain embodiments, the handle portion 314 may have an aperture that extends therethrough and the first handle section 362 may be extended through the aperture to secure the leaflet retractor tool 360 with respect to the implant insertion tool 310.

Thereafter, an end of the second handle section 364 engages a lip 366 extending from the delivery cannula 280 proximate a proximal end thereof. The second handle section 364 is pivoted with respect to the first handle section 362 as indicated by arrow 368. This pivoting motion causes the delivery cannula 280 to be urged away from the facet joint so that the leaflets 284 are retracted to within the guide cannula 260. This motion is towards the facet joint to reduce the potential that the guide cannula 260 is moved from its desired position against the facet joint during the implanting process.

Figure 33:
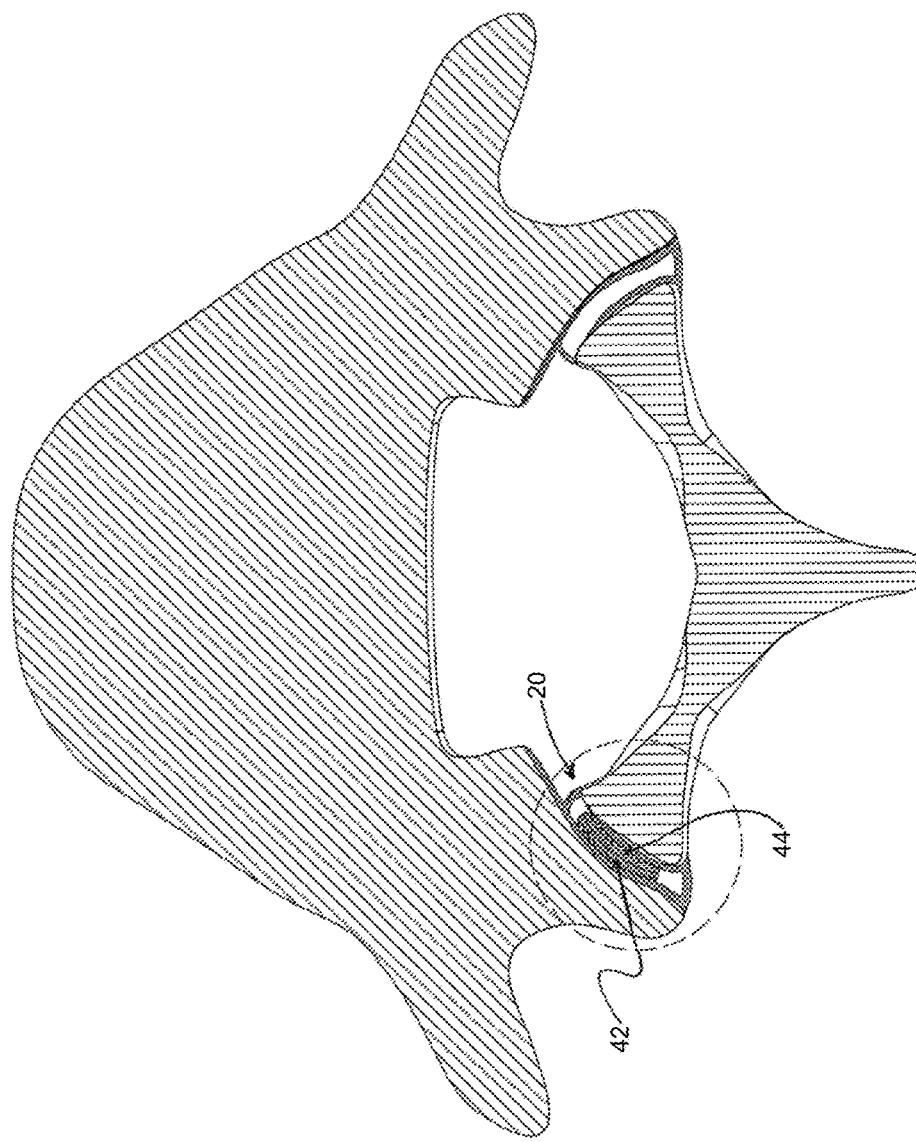
FIG. 33 is a sectional view of the resurfacing device that has been implanted in one of the facet joints.

Thereafter, the implant insertion tool 310 may be separated from the resurfacing body 46 using a gentle pull away from the resurfacing body 46 to leave the resurfacing devices 42, 44 in the facet joint as illustrated in FIG. 33. The implantation process is thereby complete. Medical imaging may be used to evaluate whether the resurfacing body has been accurately implanted prior to removing the guide cannula 260 from adjacent to the facet joint.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of resurfacing a facet joint with a facet implant system, wherein the facet joint comprises a superior facet and an inferior facet that are adjacent to each other and movable with respect to each other, wherein the method comprises:
   providing a first facet implant component comprising a first visualization marker, wherein the first visualization marker comprises a first marker section and a second marker section and wherein the first marker section is oriented at an angle with respect to the second marker section;
   implanting the first facet implant component between the superior facet and the inferior facet;
   providing a second facet implant component comprising a second visualization marker with respect to the second articulating surface, wherein the second visualization marker comprises a third marker section and a fourth marker section and wherein the third marker section is oriented at an angle with respect to the fourth marker section;
   implanting the second facet implant component between the first facet implant component and the inferior facet;
   determining a location and an orientation of the first facet implant component using an imaging technique that locates the first visualization marker; and
   determining a location and an orientation of the second facet implant component using the imaging technique to locate the second visualization marker.

2. The method of claim 1, wherein when the first facet implant component and the second facet implant component are placed in an implantation configuration, the visualization markers form a T-shape.

3. The method of claim 1, and further comprising fabricating the first visualization marker from a radio-opaque material.

4. The method of claim 1, wherein the angle between the first marker section and the second marker section is between about 60° and about 100°.

5. The method of claim 1, wherein the first facet implant component includes an insertion axis that extends between the leading edge and the trailing edge and is located intermediate a first opposing side and a second opposing side of the first facet implant component and wherein the first marker section is parallel to and positioned along the insertion axis.

6. The method of claim 1, wherein the first facet implant component comprises a first engagement surface that is opposite the first articulating surface and wherein the first facet implant component comprises teeth that extend from the first engagement surface.

7. A method of resurfacing a facet joint with a facet implant system, wherein the facet joint comprises a superior facet and an inferior facet that are adjacent to each other and movable with respect to each other, wherein the method comprises:
providing a first facet implant component comprising a first visualization marker, wherein the first visualization marker comprises a first marker section and a second marker section and wherein the first marker section is oriented at an angle with respect to the second marker section;
providing a second facet implant component comprising a second visualization marker with respect to the second articulating surface, wherein the second visualization marker comprises a third marker section and a fourth marker section and wherein the third marker section is oriented at an angle with respect to the fourth marker section;
implanting the first facet implant component and the second implant component between the superior facet and the inferior facet so that the first facet implant component is adjacent to the second implant component; and
determining a location and an orientation of the first facet implant component and the second facet implant component using an imaging technique that locates the first visualization marker and the second visualization marker.

8. The method of claim 7, wherein after the implanting, at least a portion of the first marker section overlaps the third market section and wherein after the implanting, at least a portion of the second marker section does not overlap the fourth marker section.

9. The method of claim 7, wherein when the first facet implant component and the second facet implant component are placed in an implantation configuration, the visualization markers form a T-shape.

10. The method of claim 7, and further comprising fabricating the first visualization marker and the second visualization marker from a radio-opaque material.

11. The method of claim 7, wherein the angle between the first marker section and the second marker section is between about 60° and about 100° and wherein the angle between the third marker section and the fourth marker section is between about 60° and about 100°.

12. The method of claim 7, wherein the first facet implant component includes a first insertion axis that extends between the leading edge and the trailing edge and is located intermediate a first opposing side and a second opposing side of the first facet implant component and wherein the first marker section is parallel to and positioned along the first insertion axis, wherein the second facet implant component includes a second insertion axis that extends between the leading edge and the trailing edge and is located intermediate a first opposing side and a second opposing side of the second facet implant component and wherein the third marker section is parallel to and positioned along the second insertion axis.

13. The method of claim 7, wherein the first facet implant component comprises a first engagement surface that is opposite the first articulating surface, wherein the first facet implant component comprises teeth that extend from the first engagement surface and wherein the second facet implant component comprises a second engagement surface that is opposite the second articulating surface and wherein the second facet implant component comprises teeth that extend from the second engagement surface.

14. A method of resurfacing a facet joint with a facet implant system, wherein the facet joint comprises a superior facet and an inferior facet that are adjacent to each other and movable with respect to each other, wherein the method comprises:
providing a first facet implant component comprising a first visualization marker, wherein the first visualization marker comprises a first marker section and a second marker section and wherein the first marker section is oriented at an angle with respect to the second marker section;
providing a second facet implant component comprising a second visualization marker, wherein the second visualization marker comprises a third marker section and a fourth marker section and wherein the third marker section is oriented at an angle with respect to the fourth marker section;
implanting the first facet implant component and the second implant component between the superior facet and the inferior facet so that the first facet implant component is adjacent to the second implant component, at least a portion of the first marker section overlaps the third market section and at least a portion of the second marker section does not overlap the fourth marker section; and
determining a location and an orientation of the first facet implant component and the second facet implant component using an imaging technique that locates the first visualization marker and the second visualization marker.

15. The method of claim 14, wherein when the first facet implant component and the second facet implant component are placed in an implantation configuration, the visualization markers form a T-shape.

16. The method of claim 14, and further comprising fabricating the first visualization marker and the second visualization marker from a radio-opaque material.

17. The method of claim 14, wherein the angle between the first marker section and the second marker section is between about 60° and about 100° and wherein the angle between the third marker section and the fourth marker section is between about 60° and about 100°.

18. The method of claim 14, wherein the first facet implant component includes a first insertion axis that extends between the leading edge and the trailing edge and is located intermediate a first opposing side and a second opposing side of the first facet implant component and wherein the first marker section is parallel to and positioned along the first insertion axis, wherein the second facet implant component includes a second insertion axis that extends between the leading edge and the trailing edge and is located intermediate a first opposing side and a second opposing side of the second facet implant component and wherein the third marker section is parallel to and positioned along the second insertion axis.

19. The method of claim 14, wherein the first facet implant component comprises a first engagement surface that is opposite the first articulating surface, wherein the first facet implant component comprises teeth that extend from the first engagement surface and wherein the second facet implant component comprises a second engagement surface that is opposite the second articulating surface and wherein the second facet implant component comprises teeth that extend from the second engagement surface.

* * * * *